(12) United States Patent
Gunderson et al.

(10) Patent No.: US 8,709,717 B2
(45) Date of Patent: Apr. 29, 2014

(54) GENERATION OF UNIFORM FRAGMENTS OF NUCLEIC ACIDS USING PATTERNED SUBSTRATES

(75) Inventors: Kevin Gunderson, San Diego, CA (US); Michal Lebl, San Diego, CA (US); David L. Heiner, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 13/260,205

(22) PCT Filed: Apr. 2, 2010

(86) PCT No.: PCT/US2010/029807
§ 371 (c)(1),
(2), (4) Date: Dec. 2, 2011

(87) PCT Pub. No.: WO2010/115122
PCT Pub. Date: Oct. 7, 2010

(65) Prior Publication Data
US 2012/0129704 A1    May 24, 2012

Related U.S. Application Data

(60) Provisional application No. 61/166,356, filed on Apr. 3, 2009.

(51) Int. Cl.
*C12Q 1/68* (2006.01)
*C12N 11/02* (2006.01)
*C40B 50/04* (2006.01)
*C40B 60/06* (2006.01)
*B01D 57/02* (2006.01)

(52) U.S. Cl.
USPC ............ 435/6.1; 506/26; 536/23.1; 435/177; 204/456

(58) Field of Classification Search
USPC ......................................................... 435/6.1
See application file for complete search history.

(56) References Cited

U.S. PATENT DOCUMENTS

| | | | |
|---|---|---|---|
| 5,846,832 A * | 12/1998 | Oefner et al. | 436/94 |
| 6,303,296 B1 | 10/2001 | Bensimon et al. | |
| 7,122,647 B2 * | 10/2006 | Bensimon et al. | 536/23.1 |
| 2002/0048767 A1 | 4/2002 | Bensimon et al. | |
| 2002/0137037 A1* | 9/2002 | Hornby et al. | 435/6 |
| 2004/0000561 A1 | 1/2004 | Lallemant et al. | |
| 2005/0158763 A1* | 7/2005 | Ivanisevic et al. | 435/6 |
| 2006/0133957 A1* | 6/2006 | Knapp et al. | 422/72 |
| 2007/0054272 A1 | 3/2007 | Brachet et al. | |

OTHER PUBLICATIONS

Kurosawa and Washizu (Journal of Electrostatics, 2007, vol. 65, pp. 423-430, "Dissection, acquisition and amplification of targeted position of electrostatically stretched DNA").*

(Continued)

*Primary Examiner* — Christopher M. Gross
*Assistant Examiner* — Richard L Manteuffel
(74) *Attorney, Agent, or Firm* — Hunton & Williams LLP

(57) ABSTRACT

Methods of generating nucleic acid fragments of substantially uniform length from sample nucleic acids comprising linearly stretching the sample nucleic acids over a substrate having a plurality of cleavage regions separated by relatively consistent distances, cleaving the linearly stretched sample nucleic acids at the cleavage regions, and collecting the resulting nucleic acid fragments. The method may further include collecting and concentrating the resultant nucleic acid fragments of substantially uniform length.

19 Claims, 11 Drawing Sheets

(56) References Cited

OTHER PUBLICATIONS

Assi et al., (Journal of Applied Physics, 2002, vol. 92, No. 9, pp. 5584-5586, "Massively parallel adhesion and reactivity measurements using simple and inexpensive magnetic tweezers").*

Katsura et al. ("Stretching and Cutting of a Single DNA Molecule", IEEE-EMBS Conference, 2000, Lyon France, Oct. 12, 2000, Poster 17, p. 53-57).*

Smith et al. (Science, 1996, vol. 271, pp. 795-799, Overstretching B-DNA: The elastic response of individual double-stranded and single stranded DNA molecules).*

Dimalanta et al., (Analytical Chemistry, 2004, vol. 76, pp. 5293-5301, A Microfluidic system for large DNA Molecule arrays).*

Lebofsky, et al. (2003) "Single DNA Molecule Analysis: Applications of Molecular Combing" Briefings in Functional Genomics and Proteomics 1(4): 385-396.

International Search Report for International Application No. PCT/US2010/029807, mailed Jan. 24, 2011.

* cited by examiner

GENERATION OF UNIFORM FRAGMENTS OF NUCLEIC ACIDS USING PATTERNED SUBSTRATES

CROSS-REFERENCE TO RELATED PATENT APPLICATIONS

This is a national stage application of International Patent Application PCT/US2010/029807, filed Apr. 2, 2010, which claims priority to U.S. Provisional Patent Application No. 61/166,356 filed Apr. 3, 2009, the disclosures of each of which are hereby incorporated by reference.

BACKGROUND OF THE INVENTION

1. Field of the Invention

The present invention is generally directed to methods comprising the use of patterned substrates for the generation of substantially uniform fragments of nucleic acids.

2. Description of Related Art

In most molecular biology work, short DNA fragments are used, free in solution or attached to a surface. In organisms, however, DNA molecules are, in general, very long, flexible, and dynamic. Therefore fragmentation of DNA is an important preparation step in many molecular biology applications (e.g., sequencing). Precise estimates of the insert size in the nucleic acid libraries made during sample preparation is also important for paired-end sequencing analysis as this substantially reduces the computational requirements for mapping sequence fragments back to the genome, or even determining the sequence of the genome de nova.

There exists a need in the art for a simpler method for generating nucleic acid products of substantially uniform length that are more compatible with multi-well plate formats for automation and laboratory information management system (LIMS) tracking.

BRIEF SUMMARY OF THE INVENTION

Disclosed are methods for the generation of nucleic acid fragments of substantially uniform length from a sample of one or more nucleic acids comprising linearly stretching the sample of one or more nucleic acids over a substrate having a plurality of cleavage regions separated by relatively consistent distances not varying by more than about 5-10 nucleotides in length, cleaving the linearly stretched sample nucleic acid at the cleavage regions, and collecting the resulting nucleic acid fragments.

In one embodiment of the invention, the cleavage regions of the substrate are formed using photolithographic techniques.

In another embodiment of the invention, the sample nucleic acid is linearly stretched over the substrate using a molecular combing technique. In a preferred embodiment, the molecular combing technique occurs in a flow cell using fluid flow.

In another embodiment of the invention, the sample nucleic acid is linearly stretched over the substrate using a surface-tethered nucleic acid stretching technique. In a preferred embodiment, a micron-size bead is attached to the free end of the sample nucleic acid. In a still more preferred embodiment, the surface-tethered nucleic acid stretching technique occurs in a flow cell using fluid flow. In another preferred embodiment, a magnetic bead is attached to the sample nucleic acid and magnets are used for the nucleic acid stretching.

In another embodiment of the invention, the technique is performed in parallel on a plurality of nucleic acid samples.

In one embodiment of the invention, the sample nucleic acid is linearly stretched over the substrate using a nucleic acid optical entrapment technique with an optically trapped particle that is attached to the sample nucleic acid. In one preferred embodiment, two optically trapped particles are attached to the sample nucleic acid, one to each end.

In one embodiment of the invention, the cleavage regions comprise a nuclease. In a preferred embodiment, the nuclease is selected from S1 nuclease, DNAase I, DNAase II, Mung-bean nuclease, or exonuclease I. In another preferred embodiment, the cleavage regions comprise at least one chemical hydroxyl radical generator. In a more preferred embodiment, the chemical hydroxyl radical generator is selected from 4,7-diphenyl-1,10-phenanthroline copper complex or ferrous EDTA derivatives. In one embodiment of the invention, the cleavage regions comprise an electrode. In one embodiment, the cleavage regions are spaced about 100-200 nm apart from each other.

In one embodiment of the invention, the nucleic acid fragments are at least about 300 base pairs in length. In another embodiment, the nucleic acid fragments are at least about 3 kb in length. In another embodiment, the nucleic acid fragments are at least about 30 kb in length.

In one embodiment of the invention, the sample is a DNA library. In a preferred embodiment, the DNA library is a genomic DNA library, cDNA library, eukaryotic DNA library, Achaean DNA library or prokaryotic DNA library. In another embodiment, the sample is mRNA.

In one embodiment of the invention, the substrate is a column, array, tray, or dish. In a preferred embodiment, the substrate is a bead-based or a polymer-based matrix.

In one embodiment of the invention, at least one step is automated. In another embodiment, the methods described herein further comprise collecting the resultant substantially uniform length nucleic acid fragment product(s).

The invention also contemplates a method of generating nucleic acid fragments of substantially uniform length from a sample of one or more nucleic acids comprising contacting a sample nucleic acid with an affinity ligand, linearly stretching the sample of one or more nucleic acids over a substrate having a modified region comprising a plurality of affinity ligand receptors and a plurality of cleavage regions separated by relatively consistent distances not varying by more than about 5-10 nucleotides in length, cleaving the linearly stretched sample nucleic acid at the cleavage regions, and collecting the resulting nucleic acid fragments.

In one embodiment of the invention, the affinity ligand is biotin. In one embodiment of the invention, the affinity ligand receptor is strepavidin.

In a further embodiment of the invention, the sample nucleic acid is linearly stretched over the substrate using a surface-tethered nucleic acid stretching technique. In a preferred embodiment, a micron-size bead coated with an affinity ligand is attached to the free end of the nucleic acid.

In another embodiment, the sample nucleic acid is linearly stretched over the substrate using a nucleic acid optical entrapment technique with an optically trapped particle that is attached to the sample nucleic acid. In a preferred embodiment, two optically trapped particles are attached to the sample nucleic acid, one to each end.

In one embodiment of the invention, the cleavage regions are spaced about 100-200 nm apart from each other. In a preferred embodiment, the nucleic acid fragments are at least about 300 base pairs in length. In another embodiment, the nucleic acid fragments are at least about 3 kb in length. In a further embodiment, the nucleic acid fragments are at least about 30 kb in length.

In one embodiment of the invention, the method further comprises washing said substrate. In another embodiment, the method further comprises disrupting the affinity ligand/affinity ligand receptor complexes bound to the substrate. In a preferred embodiment, the method comprises re-using the substrate to repeat the method at least once.

In one embodiment of the invention, the method comprises sequencing a nucleic acid comprising generating nucleic acid fragments of substantially uniform length from a sample of one or more nucleic acids comprising; linearly stretching the sample of one or more nucleic acids over a substrate comprising a plurality of cleavage regions separated by relatively consistent distances; cleaving the linearly stretched sample nucleic acid at the cleavage regions; collecting the resultant substantially uniform length nucleic acid fragment product; and sequencing the resultant substantially uniform length nucleic acid fragment product.

In another embodiment of the invention, the sequencing method is Maxam-Gilbert, chain-termination, dye-terminator, in vitro clonal amplification, parallelized sequencing, sequencing by ligation, sequencing by hybridization, cycle sequencing, or nanopore sequencing method.

A further embodiment of the invention, a composition comprising a substrate comprising a plurality of cleavage regions separated by relatively consistent distances. In a preferred embodiment, the composition further comprises one or more nucleic acids linearly stretched over said substrate. In a more preferred embodiment, the composition comprises nucleic acid linearly stretched over a substrate by molecular combing. In another embodiment, the composition comprises a substrate comprises a plurality of nucleic acid samples.

In another embodiment of the invention, a composition comprises a substrate comprising a plurality of cleavage regions separated by relatively consistent distances and one or more nucleic acids linearly stretched over said substrate.

In another embodiment of the invention, a kit comprising a substrate, cleavage reagent, and a device for linearly stretching nucleic acid over said substrate. The kit may further comprise buffers appropriate for the action of the cleavage reagents and linearly stretching nucleic acid over said substrate.

DETAILED DESCRIPTION OF THE INVENTION

Definitions

Figure 1:
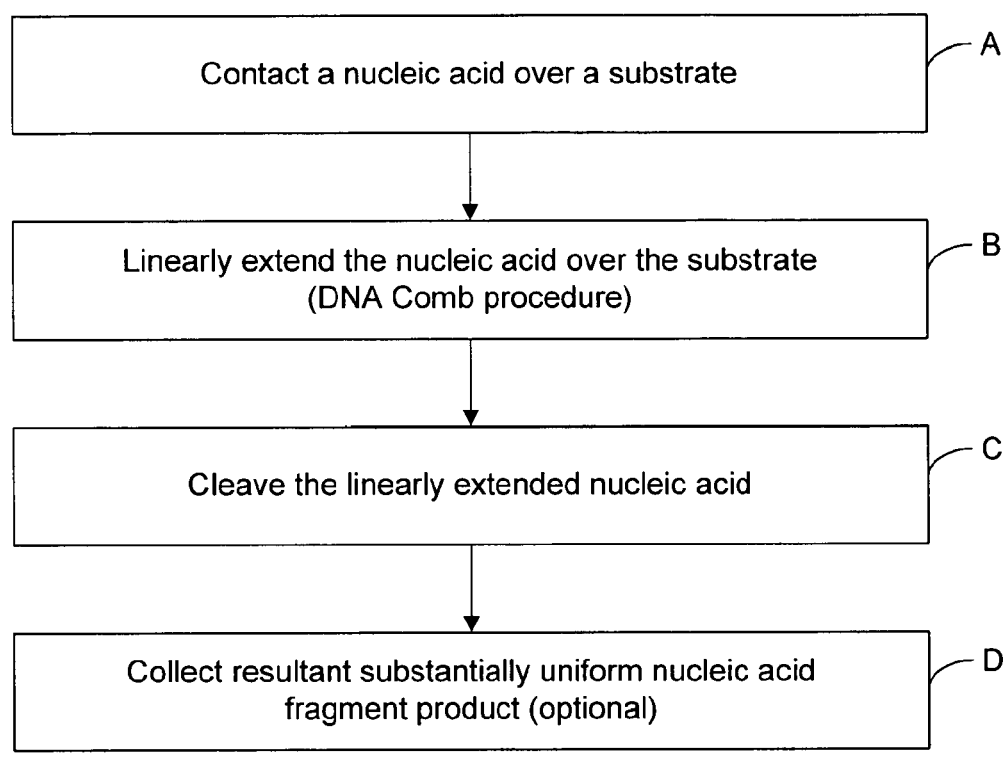
FIG. 1 is a flowchart of one embodiment of the invention.
Figure 2:
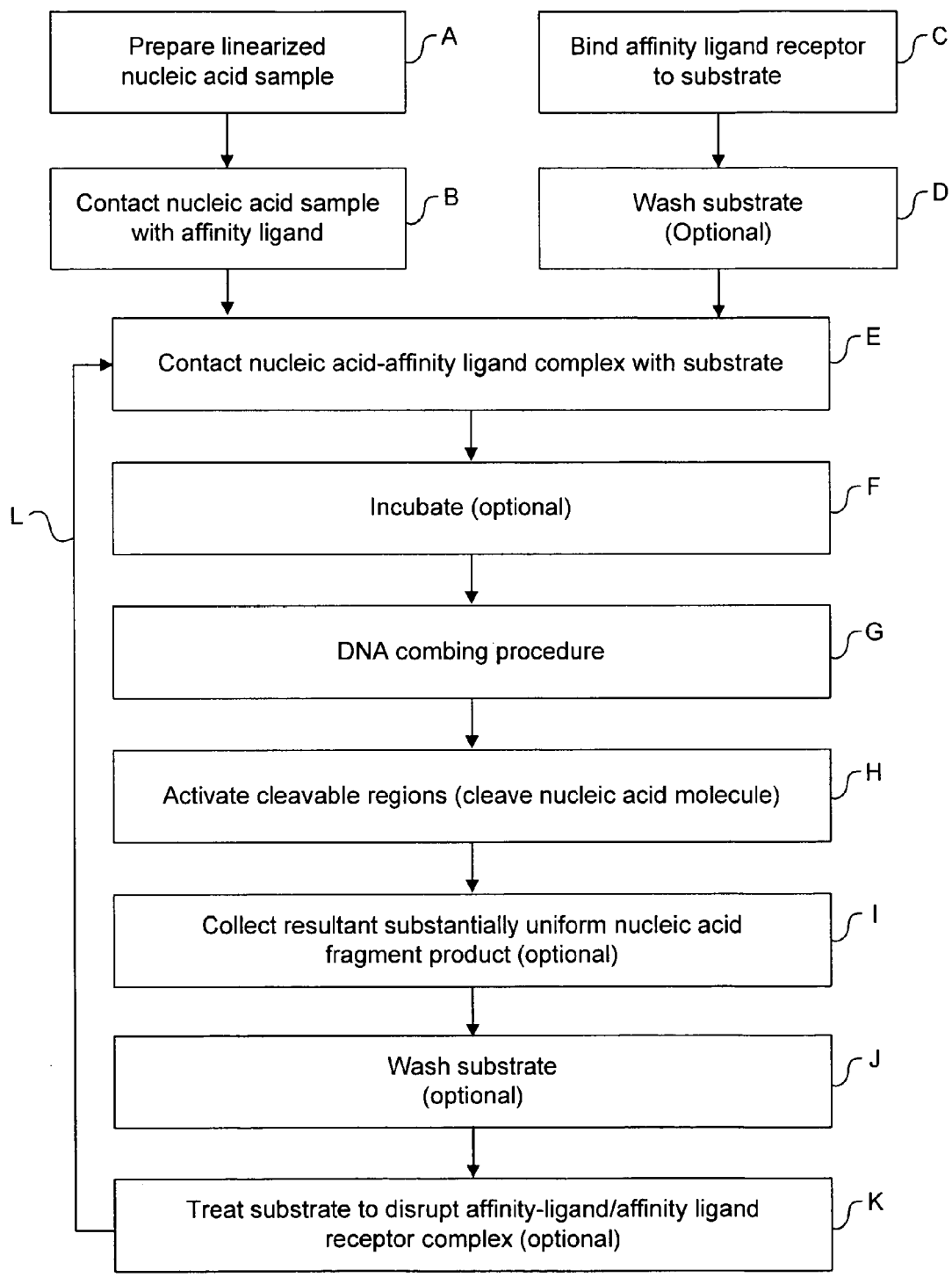
FIG. 2 is a flowchart of another embodiment of the invention.

As used herein the singular forms "a", "and", and "the" include plural referents unless the context clearly dictates otherwise. Thus, for example, reference to "a cell" includes a plurality of such cells, and so forth. All technical and scientific terms used herein have the same meaning as commonly understood to one of ordinary skill in the art to which this invention belongs unless clearly indicated otherwise.

As used herein, "affinity ligand" refers to a molecule that specifically binds to an "affinity ligand receptor." Exemplary, affinity ligand and affinity ligand receptor pairs include but are not limited to, biotin and avidin, biotin and streptavidin, receptor and ligand, antibody and ligand, antibody and antigen, and a polynucleotide sequence and its complement. One or more affinity ligands and/or affinity ligand receptors can be coupled to a substrate.

As used herein, "amplification" refers to any in vitro method for increasing the number of copies of a nucleotide sequence using a template nucleic acid having the sequence or its complement. Amplification can be carried out, for example, with a polymerase or ligase. In some embodiments, nucleic acid amplification results in the incorporation of nucleotides into a DNA and/or RNA molecule or primer thereby forming a new molecule complementary to a sample. The formed nucleic acid molecule, its template or both can be used as templates to synthesize additional nucleic acid molecules. As used herein, one amplification reaction may consist of many rounds of replication. Nucleic acid amplification reactions include, for example, polymerase chain reactions (PCR), random prime amplification, rolling circle amplification, ligase chain reaction and other methods known in the art. Examples of useful amplification methods are described in U.S. Patent Application Publication No. 2005/0037393 A1, which is incorporated herein by reference. One PCR reaction may consist of 5 to 100 "cycles" of denaturation and synthesis of a DNA molecule.

As used herein, the term "array" refers to a population of different probes, such as affinity ligand receptor molecules, that can be attached to a surface in a spatially distinguishable manner. An individual feature of an array can include a single copy of a probe, such as an affinity ligand receptor, or a population of probes, such as affinity ligand receptors, at an individual feature of the array. The population of affinity ligand receptors or other probe at each feature typically is homogenous, having a single species of affinity ligand receptor. However, in particular embodiments a heterogeneous population of affinity ligand receptors or other probes can be present at a feature. Thus, a feature need not include only a single probe species and can instead contain a plurality of different probe species.

As used herein, "complexity," when used in reference to a nucleic acid sequence, is intended to mean the total amount of unique sequence in a genome. The complexity of a sequence can be determined from the number of different words of a particular length that appear in a particular sequence, where a word is a string of contiguous nucleotides. A word can be at least about 10, 15, 20, 25, 50, 100, $1 \times 10^3$, $1 \times 10^4$, $1 \times 10^5$, $1 \times 10^6$ or more contiguous nucleotides. The complexity can be determined as the product of multiplying the number of unique sequence words in a sequence times the length of the sequence word. Generally, as the length of the sequence word is increased the complexity estimate will generally increase approaching the upper limit of the length of the genome. Thus, the complexity of a nucleic acid sequence can be equivalent to or less than the length of a single copy of a genome (e.g., the haploid sequence). For example, a nucleic acid sample can have a complexity that is at least 10%, 25%, 50%, 75%, 80%, 90%, 95%, 96%, 97%, 98%, 99%, 99.5%, 99.9% or 99.99% or more of a particular genome. Exemplary size estimates for some of the genomes that are useful in the invention are about 3.1 Gbp (human), 2.7 Gbp (mouse), 2.8 Gbp (rat), 1.7 Gbp (zebrafish), 165 Mbp (fruitfly), 13.5 Mbp (S. cerevisiae), 390 Mbp (fugu), 278 Mbp (mosquito) or 103 Mbp (C. elegans). Those skilled in the art will recognize that genomes having sizes other than those exemplified above including, for example, smaller or larger genomes can be used in a method of the invention.

As used herein, "complementary" or "complementarity" refers to the degree of base-pairing or hybridization between nucleic acids. For example, as is known to those skilled in the art, adenine (A) can form hydrogen bonds or base pair with thymine (T) or uracil (U) and guanine (G) can form hydrogen bonds or base pair with cytosine (C). Hence, A is complementary to T or U and G is complementary to C. These are the standard "Watson-Crick" base pairs occurring in the vast majority of DNA and RNA hybrids in vivo. Complementarity, when used in reference to a double stranded region of nucleic acid may be complete when all bases in the double-stranded region are base paired. Alternatively, complementarity may be "partial," in which only some of the bases in the double stranded region are matched according to the base pairing rules. The degree of complementarity between nucleic acid strands has an effect on the efficiency and strength of hybridization between nucleic acid strands. "Complementary" sequences can also include, or be formed entirely from, non-Watson-Crick base pairs and/or base pairs formed from non-natural and modified nucleotides, in so far as the above requirements with respect to their ability to hybridize are fulfilled.

As used herein, "hybridization" refers to the physical interaction of complementary (including partially complementary) polynucleotide strands by the formation of hydrogen bonds between complementary nucleotides when the strands are arranged antiparallel to each other. Hybridization and the strength of hybridization (e.g., the strength of the association between polynucleotides) is impacted by many factors well known in the art including the degree of complementarity between the polynucleotides, and the stringency of the conditions involved, which is affected by such conditions as the concentration of salts, the presence of other components (e.g., the presence or absence of polyethylene glycol), the molarity of the hybridizing strands and the G+C content of the polynucleotide strands, all of which results in a characteristic melting temperature ($T_m$) of the formed hybrid. The terms "hybridization (hybridize)" and "binding," when used in reference to nucleic acids, can be used interchangeably and can refer to the process by which single strands of nucleic acid sequences form double-helical segments through hydrogen bonding between complementary nucleotides. "Hybrid," "duplex," and "complex," when used in reference to nucleic acids, can also be used interchangeably herein refering to a double-stranded nucleic acid molecule formed by hybridization (e.g., DNA-DNA, DNA-RNA, and RNA-RNA species).

As used herein, "isolated" will mean material removed from another material in a sample. For example, a material can be removed from its original environment in which it naturally occurs, and thus is altered by the hand of man. Isolated material may be, for example, exogenous nucleic acid included in a vector system, exogenous nucleic acid contained within a host cell, or any material which has been removed from its original environment and thus altered by the hand of man.

As used herein, "label" refers to any atom or molecule that can be used to provide a detectable (preferably quantifiable) signal. Particularly useful labels can be attached to a molecule of interest such as a nucleic acid or protein. Labels may provide signals detectable by such non-limited techniques as fluorescence, radioactivity, colorimetry, gravimetry, X-ray diffraction or absorption, magnetism, and enzymatic activity.

As used herein, "nucleic acid" includes polymers of deoxyribonucleotides or ribonucleotides in either single- or double-stranded form. The term can include such polymers that are composed of monomers (nucleotides) containing a sugar, phosphate and a base that is either a purine or pyrimidine. Unless specifically limited, the term encompasses nucleic acids containing analogs of natural nucleotides that have similar binding properties as the reference nucleic acid and/or nucleic acids having non-native backbones such as protein nucleic acids. In particular embodiments, nucleotide analogs are also metabolized in a manner similar to naturally occurring nucleotides. Reference to a particular nucleic acid sequence can implicitly refer to its complementary sequences as well as the reference sequence explicitly indicated. For example, teaching related to amplifying a nucleic acid sequence will be understood to include embodiments where one or more copies of the sequence, its complement or both are produced, unless explicitly stated to the contrary.

As used herein, "nucleotide" and "nucleotide base" refers to a base-sugar-phosphate combination. Nucleotides are monomeric units of a nucleic acid sequence (DNA and RNA). The term nucleotide includes ribonucleoside triphosphate ATP, UTP, CTP, GTP and deoxyribonucleoside triphosphates such as dATP, dCTP, dITP, dUTP, dGTP, dTTP, or derivatives thereof. "Nucleotide" as used herein also refers to dideoxyribonucleoside triphosphates (ddNTPs) and their derivatives including, but not limited to, ddATP, ddCTP, ddGTP, ddITP, and ddTTP. In one embodiment of the invention, a "nucleotide" may be unlabeled or detectably labeled by well known techniques. Detectable labels include, but are not limited to, radioactive isotopes, fluorescent labels, chemiluminescent labels, bioluminescent labels, and enzyme labels.

As used herein, "nucleic acid fragment" refers to a synthetic or natural molecule comprising a covalently linked sequence of nucleotides. The nucleotides can be joined by a phosphodiester bond between the 3' position of the deoxyribose or ribose of one nucleotide and the 5' position of the deoxyribose or ribose of the adjacent nucleotide. A nucleic acid fragments can include natural (e.g., a, G, C, T or U) or modified bases (e.g., 7-deazaguanosine, inosine). In addition, the bases in a nucleic acid fragments can be joined by a linkage other than a phosphodiester bond, so long as it does not interfere with hybridization of the nucleic acid fragment. Thus, nucleic acid fragments can be peptide nucleic acids in which one or more of the constituent bases are joined by peptide bonds rather than phosphodiester linkages.

As used herein, "nuclease" refers to any enzyme that cleaves nucleic acids. Nucleases belong to a class of enzymes called hydrolases and are usually specific in action, ribonucleases acting preferentially upon ribonucleic acids (RNA) and deoxyribonucleases acting preferentially upon deoxyribonucleic acids (DNA). Some enzymes having a general action (e.g., phosphoesterases, which hydrolyze phosphoric acid esters) can be called nucleases because nucleic acids are susceptible to their action.

Figure 3:
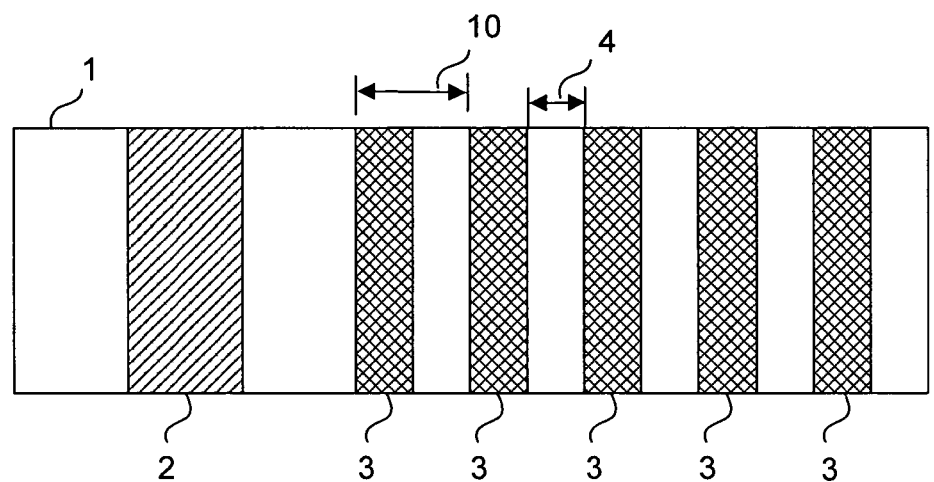
FIG. 3 shows an exemplary substrate (e.g., slide) with a patterned (e.g., striped) cleavage region 3 spaced by a gap 4 and a pitch 10 (e.g., at least about 100 nm to 10 μm) and modified (e.g., silananized) region 2, according to one embodiment of the invention. The cleavage region can be patterned by photolithographic techniques.
Figure 4:
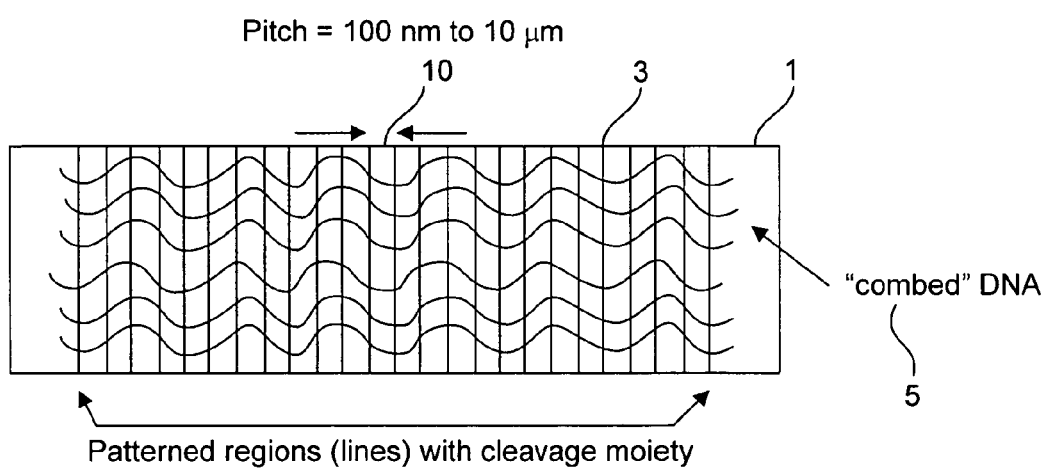
FIG. 4 shows an exemplary substrate 1 (e.g., glass slide) with a patterned (e.g., striped) cleavage region 3 with a pitch 10 of at least about 100 nm to 10 μm, and transverse "combed DNA" 5. The cleavage region can be patterned by photolithographic techniques. Once combed out, the cleavage can be activated leading to the substantially uniform fragmentation of the combed nucleic acid (or depending on spacing, any distribution may be achieved), according to one embodiment of the invention.

As used herein, "pitch" refers to the distance between corresponding points on two juxtaposed cleavage regions on a substrate having a repeated pattern of cleavage regions. For example, the corresponding points can be the centers of two adjacent cleavage regions (e.g., center to center distance). In another example, the pitch can be measured from the left most edge of a first cleavage region to the left most edge of an adjacent cleavage region such that the distance includes the gap between the cleavage regions as well as the length of one of the cleavage regions. The pitch can be, for example, at least about 1 nm to 1,000 μm. See e.g., FIGS. 3 and 4.

As used herein, "primer" refers to a single-stranded oligonucleotide that is extended by covalent bonding of nucleotide monomers during amplification or polymerization of a nucleic acid molecule. A primer can be naturally occurring as in a purified restriction digest or produced synthetically, which is capable of acting as a point of initiation of sample-dependent nucleic acid synthesis. The primer may be either single-stranded or double-stranded and, in particular embodiments, must be sufficiently long to prime the synthesis of the desired extension product in the presence of the chosen polymerase. The exact length of the primer will depend upon many factors, including hybridization and polymerization temperatures, source of primer and the method used. For example, a primer can comprise about at least 15-75 nucleotides, although it may contain fewer or more nucleotides. The factors involved in determining the appropriate length of primer for a particular application are readily known to one of ordinary skill in the art.

As used herein, "probe," when used in reference to a target nucleic acid, refers to a molecule, such as a single stranded polynucleotide, that may be used to bind to and/or isolate the target nucleic acid.

As used herein, "sample" refers to material that includes double-stranded or single-stranded nucleic acid molecules which are to be cleaved, amplified, hybridized, purified, isolated, synthesized, sequenced and/or otherwise targeted for a specific use. Samples can include all or a portion of a gene, a regulatory sequence, genome, genomic DNA, cDNA, transcriptome, RNA including mRNA or rRNA. It may be any length, with the understanding that longer sequences are more specific.

For instance, a sample can be a "library" or "nucleic acid library," a set of nucleic acid molecules (e.g., circular or linear) representative of all or a significant portion of the DNA content of an organism (e.g., "genomic library") or a set of nucleic acid molecules representative of all or a significant portion of the expressed genes (e.g., "cDNA library") in a cell, tissue, organ, or organism. A nucleic acid library may be a eukaryotic cDNA library, eukaryotic genomic library, prokaryotic genomic library, random semi-random nucleic acid library, or semi-random nucleic acid library. Such libraries may or may not be contained in one or more vectors.

As used herein "solid support," "support," and "substrate" refers to any material that provides a solid or semi-solid structure with which another material can be attached including but not limited to smooth supports (e.g., metal, glass, plastic, silicon, and ceramic surfaces) as well as textured and porous materials. Substrate materials include, but are not limited to acrylics, carbon (e.g., graphite, carbon-fiber), cellulose (e.g., cellulose acetate), ceramics, controlled-pore glass, cross-linked polysaccharides (e.g., agarose or SEPHAROSE®), gels, glass (e.g., modified or functionalized glass), gold (e.g., atomically smooth Au(111)), graphite, inorganic glasses, inorganic polymers, latex, metal oxides (e.g., $SiO_2$, $TiO_2$, stainless steel), metalloids, metals (e.g., atomically smooth Au(111)), mica, molybdenum sulfides, nanomaterials (e.g., highly oriented pyrolitic graphite (HOPG) nanosheets), nitrocellulose, NYLON®, optical fiber bundles, organic polymers, paper, plastics, polacryloylmorpholide, poly(4-methylbutene), poly(ethylene terephthalate), poly(vinyl butyrate), polybutylene, polydimethylsiloxane (PDMS), polyethylene, polyformaldehyde, polymethacrylate, polypropylene, polysaccharides, polystyrene, polyurethanes, polyvinylidene difluoride (PVDF), quartz, rayon, resins, rubbers, semiconductor material, silica, silicon (e.g., surface-oxidized silicon), sulfide, and TEFLON®.

Substrates need not be flat and can include any type of shape including spherical shapes (e.g., beads) or cylindrical shapes (e.g., fibers). Materials attached to solid supports may be attached to any portion of the solid support (e.g., may be attached to an interior portion of a porous solid support material).

Substrates may be patterned, where a pattern (e.g., stripes, swirls, lines, triangles, rectangles, circles, arcs, checks, plaids, diagonals, arrows, squares, or cross-hatches) is etched, printed, treated, sketched, cut, carved, engraved, imprinted, fixed, stamped, coated, embossed, embedded, or layered onto a substrate. The pattern can comprise one or more cleavage regions or modified regions on the substrate.

A biological material is "attached" to a substrate when it is associated with the solid substrate through a stable chemical or physical interaction. In some preferred embodiments, the attachment is through a covalent bond. However, attachments need not be covalent or permanent. In one embodiment, materials are attached to a substrate through a "spacer molecule" or "linker group." Such spacer molecules are molecules that have a first portion that attaches to the biological material and a second portion that attaches to the substrate. Thus, when attached to the substrate, the spacer molecule separates the substrate and the biological materials, but is attached to both. Methods of attaching biological material (e.g., nucleic acid, affinity ligand receptor, enzyme, chemical hydroxyl radical generator) to a substrate are well known in the art, and include but are not limited to chemical coupling.

As used herein, the term "surface" refers to a part of a support structure (e.g., substrate) that is accessible to contact with reagents, beads or analytes. The surface can be substantially flat or planar. Alternatively, the surface can be rounded or contoured. Exemplary contours that can be included on a surface are wells, depressions, pillars, ridges, channels or the like. Exemplary materials that can be used as a support structure include, but are not limited to acrylics, carbon (e.g., graphite, carbon-fiber), cellulose (e.g., cellulose acetate), ceramics, controlled-pore glass, cross-linked polysaccharides (e.g., agarose or SEPHAROSE®), gels, glass (e.g., modified or functionalized glass), gold (e.g., atomically smooth Au(111)), graphite, inorganic glasses, inorganic polymers, latex, metal oxides (e.g., $SiO_2$, $TiO_2$, stainless steel), metalloids, metals (e.g., atomically smooth Au(111)), mica, molybdenum sulfides, nanomaterials (e.g., highly oriented pyrolitic graphite (HOPG) nanosheets), nitrocellulose, NYLON®, optical fiber bundles, organic polymers, paper, plastics, polacryloylmorpholide, poly(4-methylbutene), polyethylene terephthalate), poly(vinyl butyrate), polybutylene, polydimethylsiloxane (PDMS), polyethylene, polyformaldehyde, polymethacrylate, polypropylene, polysaccharides, polystyrene, polyurethanes, polyvinylidene difluoride (PVDF), quartz, rayon, resins, rubbers, semiconductor material, silica, silicon (e.g., surface-oxidized silicon), sulfide, and TEFLON®. A single material or mixture of several different materials can form a surface useful in the invention. The terms "surface" and "substrate" are used interchangeably herein.

General Method(s) of the Invention

The methods described herein are generally methods comprising the use of patterned substrates for the generation of substantially uniform fragments of nucleic acids, preferably in an automated format. Generally, a substrate can be coated with the octenyl carbon chain product of a gas-phase silanization reaction that is dipped into a buffered nucleic acid solution. Nucleic acid strand ends can bind to the hydrophobic surface in a pH-dependent manner and can be stretched as the substrate (e.g., slide) is pulled from the solution at a constant speed (e.g., 100, 200, 300, 400, 500, 600, 700, 800, or 1,000 μm/s), producing fixed DNA strands aligned in parallel over the surface of the slide.

The method may further include collecting, concentrating, or packaging the resultant substantially uniform nucleic acid fragments. The method may further comprise precipitating, washing, gel-purifying, or lyophilizing the substantially uniform nucleic acid fragments. In particular embodiments the resultant substantially uniform nucleic acid fragments are collected as a pool. The pool can be collected such that individual fragments are released simultaneously or sequentially into a common mixture. The fragments in a pool need not have been individually isolated following cleavage. A pool can have a variety of different nucleic acid fragments (e.g., fragments with different sequences). The number of different fragments in the pool can be, for example, at least about 10, 50, 100, $1 \times 10^3$, $1 \times 10^4$, $1 \times 10^5$, $1 \times 10^6$, $1 \times 10^7$, $1 \times 10^8$, $1 \times 10^9$ or more. The total sequence complexity of the pool can be the same as the sequence complexities set forth elsewhere herein, for example, in the context of genome complexity.

A pool of nucleic acid fragments can be subjected to one or more further manipulations or steps without subsequently isolating individual fragments. For example, a pool of nucleic acid fragments can be subjected to a sequencing method set forth herein or otherwise known in the art. However, if desired one or more fragments in a pool can be isolated at a desired step of the methods set forth herein. Standard isolation methods known in the art such as precipitation, gel electrophoresis, chromatographic techniques or the like can be used including, but not limited to those set forth in Sambrook and Russell (2001) "Molecular Cloning: A Laboratory Manual." $3^{rd}$ Edition; Ausubel, et al. (2002) *Short Protocols in Molecular Biology*. $5^{th}$ Edition; and Tijssen (1993) *Techniques in Biochemistry and Molecular Biology—Hybridization with Nucleic Acid Probes* "Overview of principles of hybridization and the strategy of nucleic acid assays" each of which are herein incorporated by reference in their entireties.

Optional steps include washing, blocking, incubation, and repetition of any one or more, or all of the steps of the method. The method as described herein can be partially or fully automated, and robotic high throughput systems are preferred. Further, the substrate may be treated (e.g., subjected to conditions) to disrupt the affinity ligand-affinity ligand receptor. The substrate can be washed and reused.

For example, components of the invention can be applied to appropriate liquid-phase, combinatorial nucleic acid synthesis protocols, to other solid- or liquid-phase nucleic acid protocols, or to any combination thereof.

In one embodiment of the invention, very long nucleic acid fragments can be generated by making long nucleic acid fragments by ligation, thermocycled amplification followed by size selection including gel selection which would be used to generate a large pool of polymers for use in multiple assays. The ratio of nucleic acid fragments/substrate can be optimized to maximize the yield while minimizing the overlap of pattern.

Embodiments of the present invention provide kits comprising a substrate, cleavage reagent, and a device for linearly stretching nucleic acid over said substrate described herein. These kits may be used in the methods disclosed herein. A kit can further include reagents for attaching nucleic acids to the surface of a substrate. Exemplary reagents are set forth herein or will be recognized by those skilled in the art based on the description of methods for attaching nucleic acids as set forth herein. In another embodiment, the kits may include instructions, directions, labels, warnings, or information pamphlets. The kit can further include an enzyme and cofactors such as activators or inhibitors appropriate for controlling the action of the enzyme.

Molecular Combing (e.g., Chromosome Combing, Nucleic Acid Combing)

In one embodiment of the invention, the general method described herein comprises the step of linearly stretching one or more sample nucleic acids transversely over a patterned cleavage regions (a technique also referred to herein as molecular combing.). Linear stretching of one or more sample nucleic acids can be accomplished by molecular combing (e.g., chromosome combing, nucleic acid combing) a process whereby single nucleic acid molecule binds by one or both extremities (or regions proximal to one or both extremity) to a modified surface (e.g., silanised glass) and are then substantially uniformly stretched and aligned by a receding air/water interface. The stretching method has a high resolution ranging from a few kilobases to megabases. Schurra and Bensimon (2009) "Combing genomic DNA for structure and functional studies." Methods Mol. Biol. 464: 71-90; See also U.S. Pat. No. 7,122,647, both of which are herein incorporated by reference in their entirety.

In particular embodiments, molecular combing is performed by a fluid flow method or by application of weak forces such as electrophoresis or receding meniscus.

Fluid Flow Stretching

Molecular combing can be done by combing by capillary flow or combing by force flow. In a fluid flow embodiment, nucleic acid is stretched in solution as it flows through a microfluidic channel or it is stretched on a solid surface. Generally microfluidic or nanofluidic flow chambers can be used.

The percentage of fully-stretched nucleic acid molecules depends on the length of the nucleic acid molecules. Generally, the longer the nucleic acid molecules, the easier it is to achieve a complete stretching. For example, according to Conti, et al., over 40% of a 10 kb DNA molecules could be routinely stretched with some conditions of capillary flow, while only 20% of a 4 kb molecules could be fully stretched using the same conditions. For shorter nucleic acid fragments, the stretching quality can be improved with the stronger flow induced by dropping coverslips onto the slides. However, this approach may shear longer nucleic acid fragments into shorter pieces and is therefore may not suitable for stretching longer molecules. See e.g., Conti, et al. (2003) *Current Protocols in Cytometry* John Wiley & Sons, Inc. and Gueroui, et al. (Apr. 30, 2002) "Observation by fluorescence microscopy of transcription on single combed DNA." PNAS 99(9): 6005-6010, both of which are hereby incorporated by reference in their entirety. See also WO 97/18326 Bensimon, et al. (May 22, 1997) and WO 00/73503 Bensimon, et al. (Dec. 7, 2000), both of which are hereby incorporated by reference in their entirety. Lebofsky and Bensimon (2003) "Single DNA molecule analysis: applications of molecular combing." Brief Funct. Genomic Proteomic 1: 385-96, hereby incorporated by reference in its entirety.

Weak Force Stretching

Figure 5:
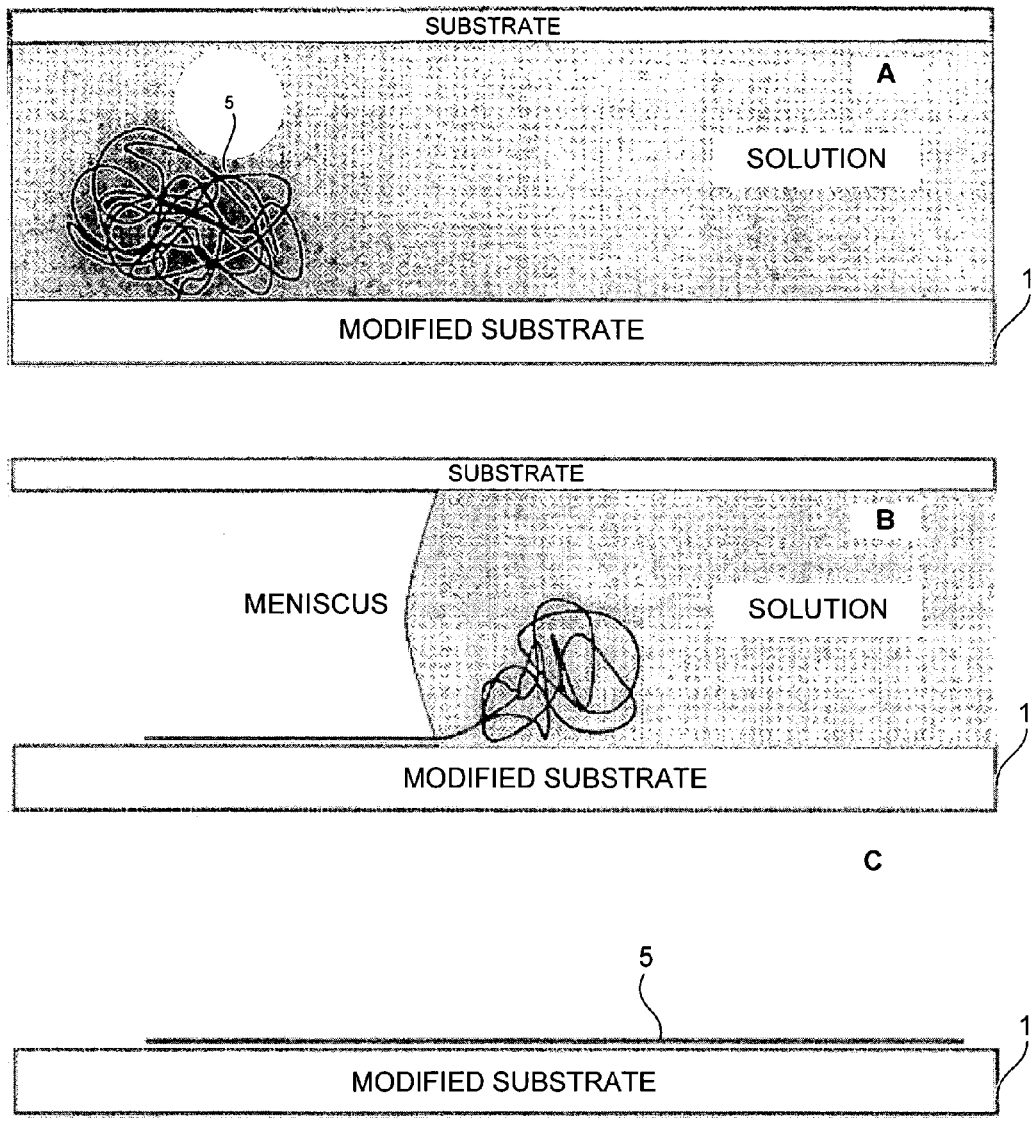
FIG. 5 depicts a receding meniscus method according to one embodiment of the invention. The substrate (e.g., glass) is treated with CDMOS (chlorodimethyloctadecylsilane) for 30 minutes at 90° C. (A) One or more sample nucleic acids 5 are introduced to a solution between two substrates, a modified substrate and an unmodified substrate. (B) The sample nucleic acid molecule attaches to the modified substrate 1 at one end and is stretched by various weak forces (e.g., electric force, surface tension, or optical force). The anchored sample nucleic acid molecules are stretched by a receding meniscus (e.g., nitrogen gas flow). (C) The substrate is dried yielding a sample nucleic acid molecule linearly stretched on the modified substrate.
Figure 6:
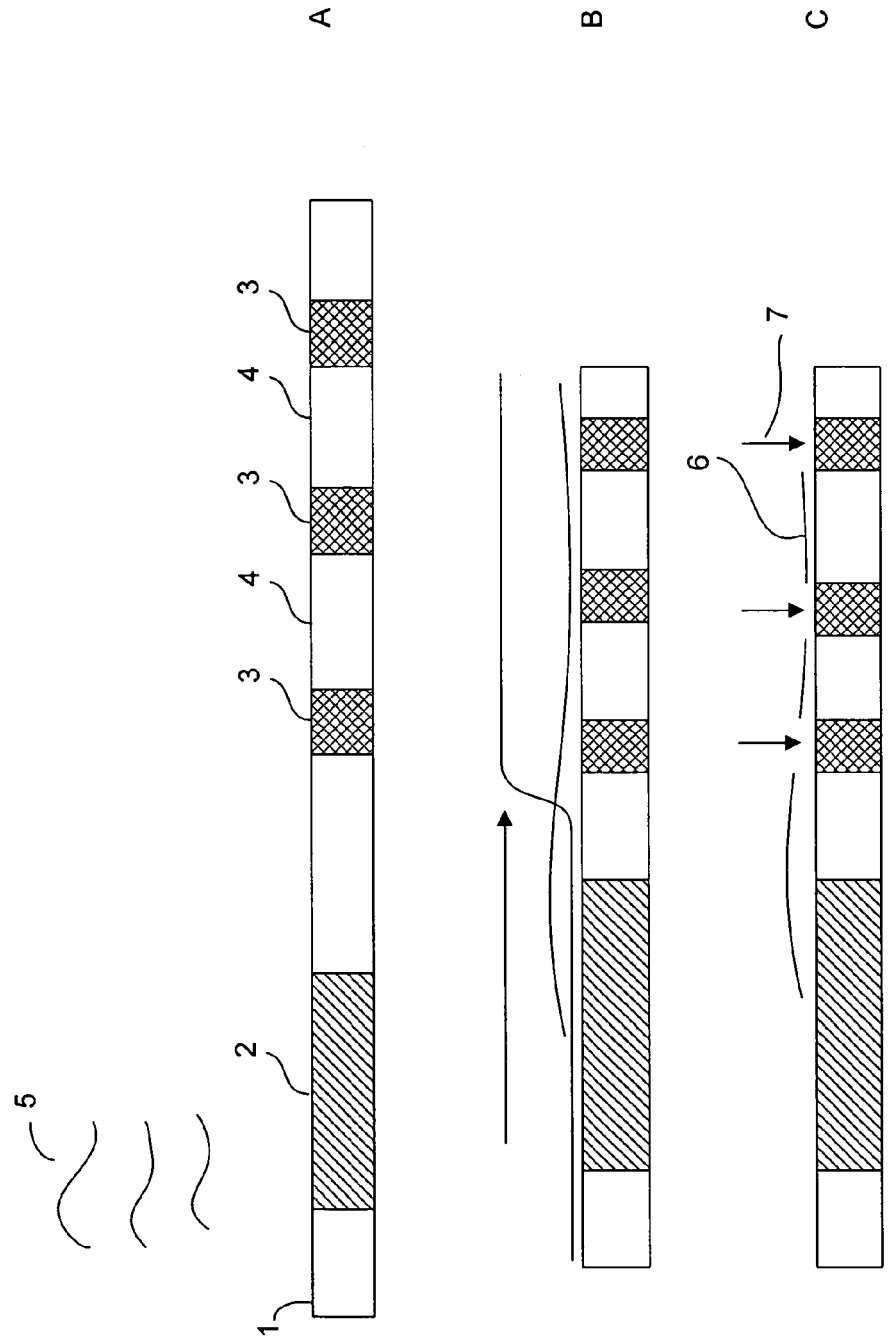
FIG. 6 depicts (A) contacting nucleic acid molecules 5 with a substrate 1 having a modified region (e.g., silanized) 2, and several cleavage regions 3, wherein the cleavage regions have a gap 4; (B) "combing DNA" on the substrate 1; and (C) cleaving 7 the nucleic acid molecule bound to an affinity ligand or particle (e.g., bead) to form substantially uniform nucleic acid fragments 6, according to one embodiment of the invention. Optionally, the substantially uniform nucleic acid fragments 6 can be collected by washing the substrate with a solution (e.g., buffer).
Figure 7:
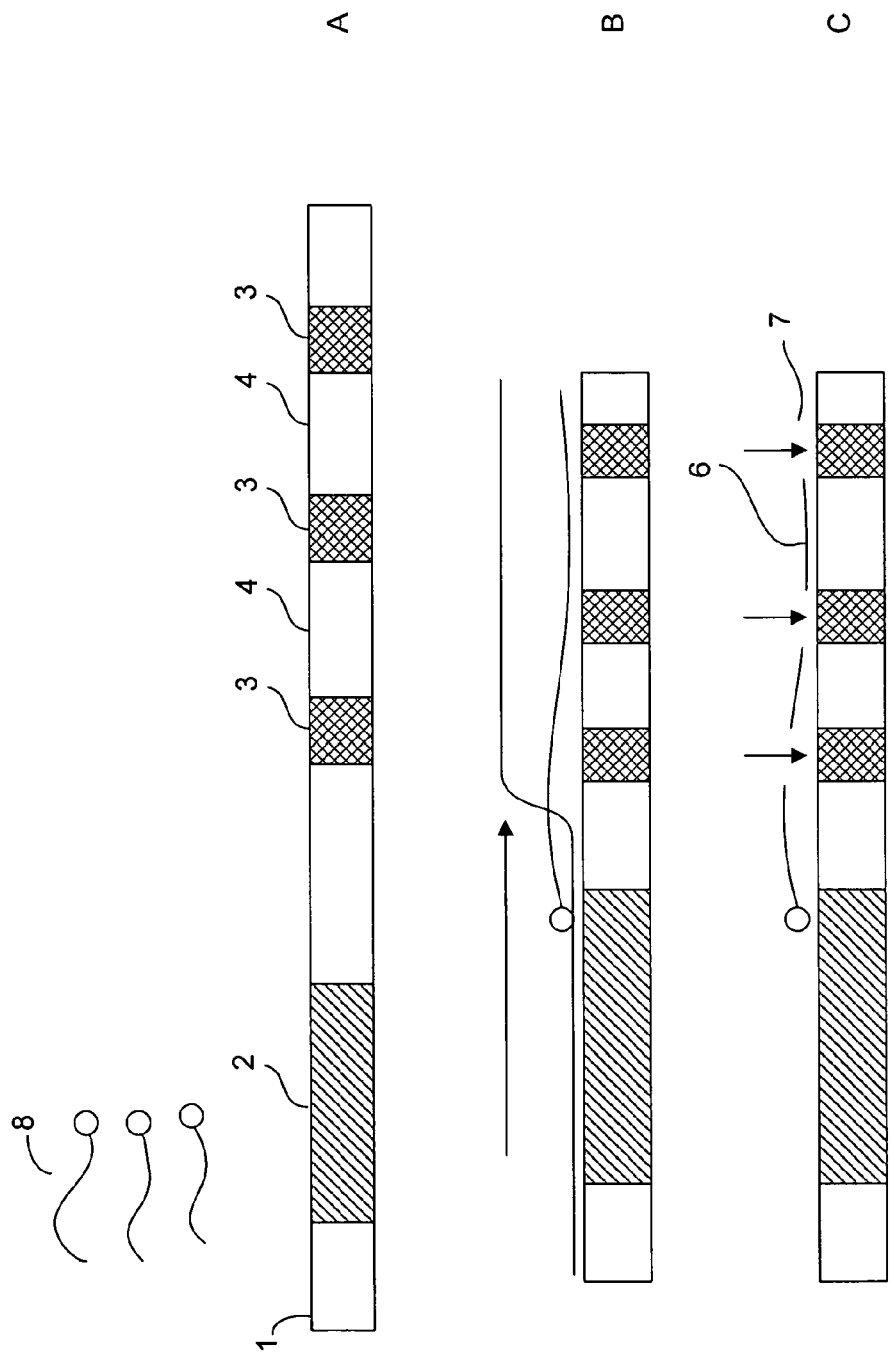
FIG. 7 depicts (A) contacting nucleic acid molecules bound to an affinity ligand or particle (e.g., bead) 8 with a substrate 1 having a modified region (e.g., silanized) 2, and several cleavage regions 3, wherein the cleavage regions have a pitch 4; (B) "combing DNA" on the substrate 1; and (C) cleaving 7 the nucleic acid molecule bound to an affinity ligand or particle (e.g., bead) to form substantially uniform nucleic acid fragments 6, according to one embodiment of the invention. Optionally, the substantially uniform nucleic acid fragments 6 can be collected by washing the substrate with a solution (e.g., buffer).
Figure 8:
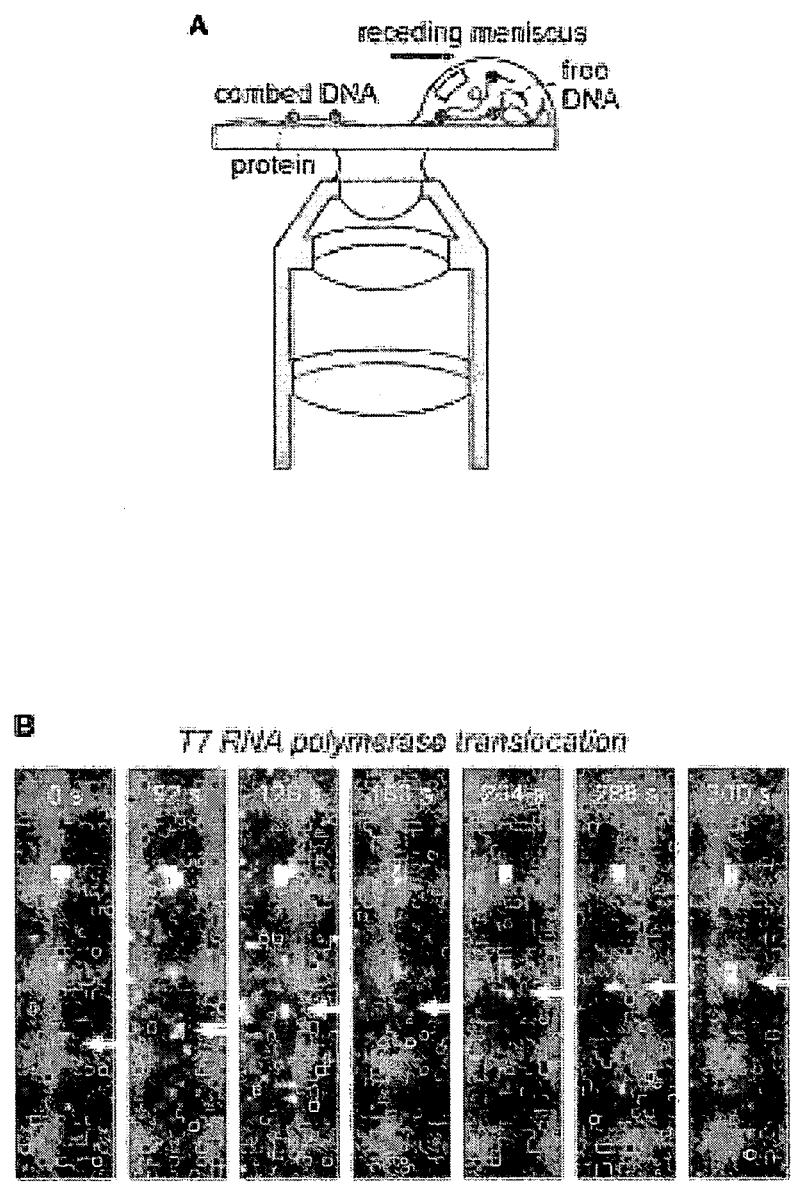
FIG. 8 depicts (A) immobilizing a nucleic acid molecule on a surface by a combing procedure. Nucleic acid can be stretched and immobilized using hydrophobic silanized glass surfaces and a receding air/water interface. After rehydration of the sample the DNA stays firmly attached to the glass slide. Combing can also be achieved using fluid flow which results in lower stretching forces. (B) Depicts the visualization in real time the motion of T7 RNAP along combed nucleic acid strands. The directional movement of the T7 RNAP elongation complex along a nucleic acid molecule is observed using the incorporation of fluorescent UTP into RNA strand, according to one embodiment of the invention. See van Mameren, et al. (2008) "See me, feel me: Methods to concurrently visualize and manipulate single DNA molecules and associated proteins." Nucleic Acids Research 36: 4381-4389, herein incorporated by reference in its entirety.
Figure 9:
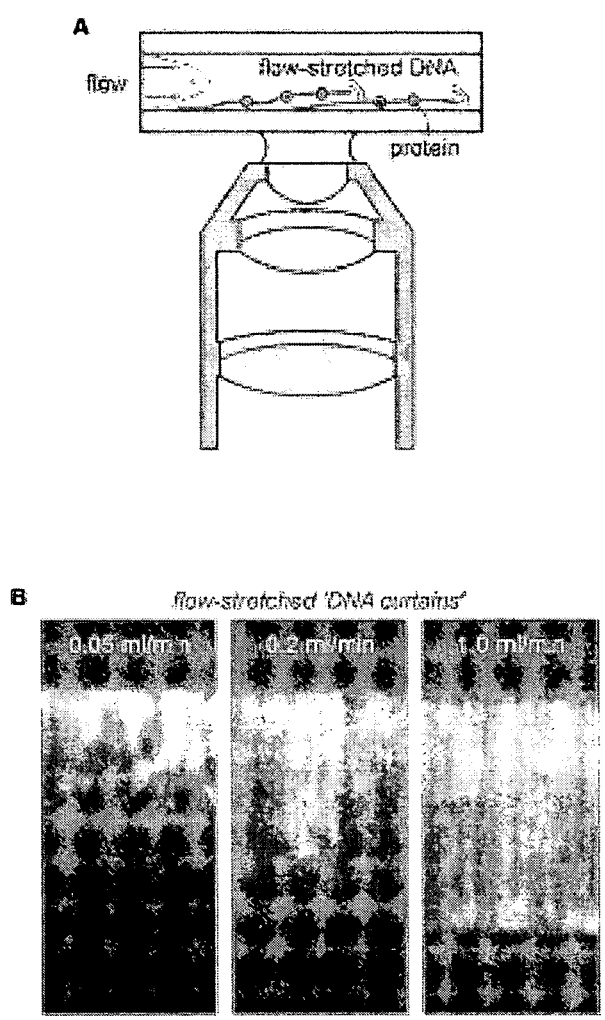
FIG. 9 depicts a schematic of one of the embodiments of the invention comprising stretching of surface-tethered nucleic acid using continuous flow, according to one embodiment of the invention. (A) Nucleic acid is attached to the glass surface with one end. To overcome the entropic forces that keep the nucleic acid compact a continuous solvent flow is applied, stretching the nucleic acid. Visualization of nucleic acid or associated proteins can be realized using fluorescence microscopy. (B) The extent of nucleic acid stretching depends on the flow rates. Simultaneous observation and cleavage of a plurality nucleic acid molecules is also possible, according to one embodiment of the invention. See van Mameren, et al. (2008) "See me, feel me: Methods to concurrently visualize and manipulate single DNA molecules and associated proteins." Nucleic Acids Research 36: 4381-4389, herein incorporated by reference in its entirety.
Figure 10:
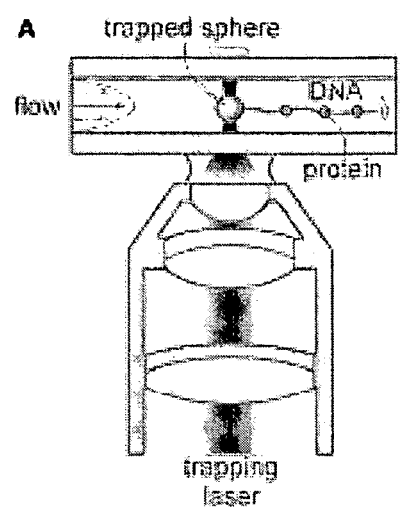
FIG. 10 depicts stretching of nucleic acid held on one side in an optical trap using continuous flow, according to one embodiment of the invention. (A) Schematic of the assay. The nucleic acid is attached to a bead with one end, the bead is held in an optical trap. A continuous solvent flow is applied stretching the nucleic acid. The nucleic acid or associated proteins can be visualized using fluorescence microscopy. (B) Application of one embodiment of the invention to the formation of RecA filaments. The nucleic acid was incubated with fluorescent RecA and filament formation was monitored by fluorescence, according to one embodiment of the invention. See van Mameren, et al. (2008) "See me, feel me: Methods to concurrently visualize and manipulate single DNA molecules and associated proteins." Nucleic Acids Research 36: 4381-4389, herein incorporated by reference in its entirety.
Figure 10:
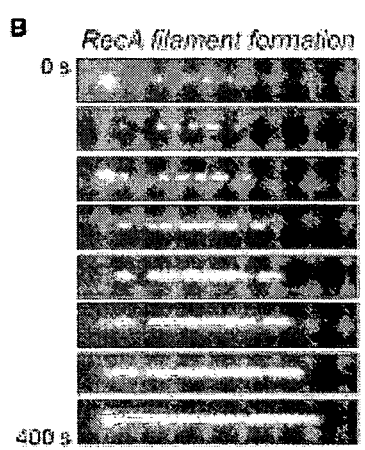
Figure 11:
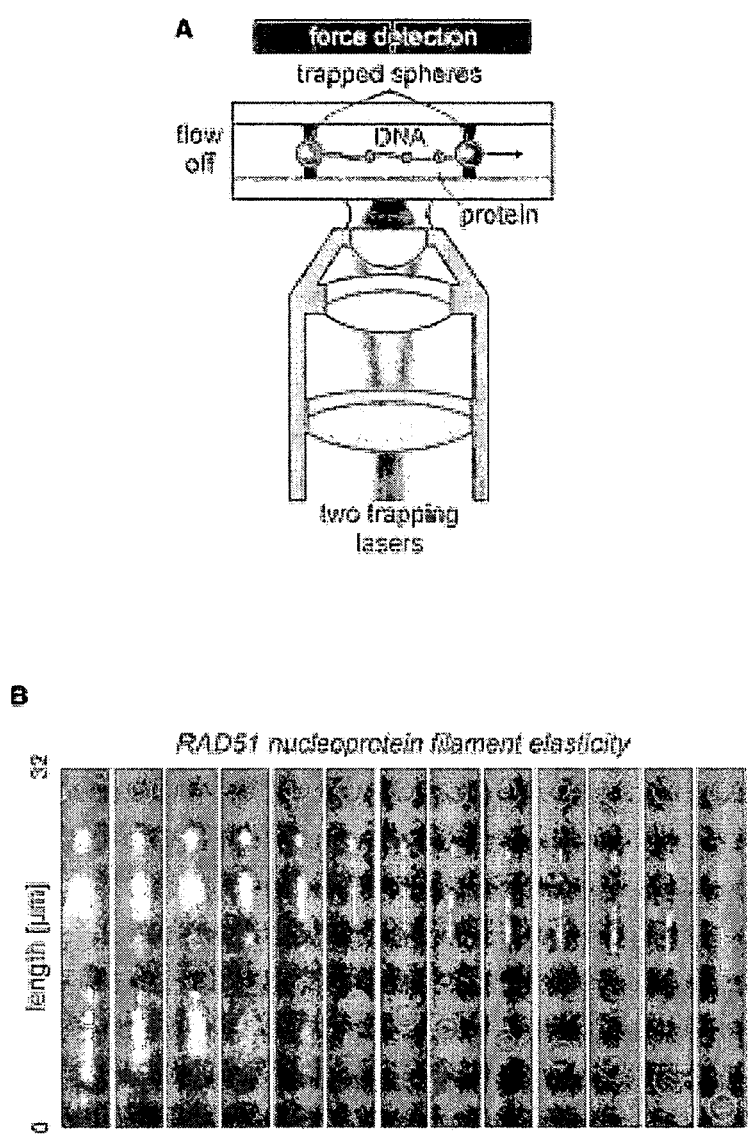
FIG. 11 depicts enhanced control using two force-measuring optical traps, according to one embodiment of the invention. (A) Schematic of the dual-trap assay. Two traps can be generated from a single laser source by splitting into two orthogonal polarizations, which may be independently steered in the sample. After suspending a single nucleic acid molecule in between two trapped beads, the nucleic acid can be manipulated without the application of force. In addition, optical tweezers can be employed to quantitatively detect the forces exerted on the nucleic acid. The fluorescence from DNA-staining dyes or fluorescently labeled DNA-binding proteins may be detected using a CCD camera. (B) Assay of the elasticity of (fluorescently labeled) RAD51 nucleoprotein filaments formed on double-stranded nucleic acid. One nucleic acid molecule is suspended between two optically trapped beads (dark circles); a second molecule was tethered from the lower bead and freely diffused once buffer flow is switched off. By increasing the distance between the traps, tension can be applied to the suspended nucleic acid in a controlled manner. The differentiated stretching of the fluorescent, RAD51-coated segments and the dark, uncoated segments can be directly seen. The increasing suppression of thermally excited diffusion of the nucleic acid can be readily observed. See van Mameren, et al. (2008) "See me, feel me: Methods to concurrently visualize and manipulate single DNA molecules and associated proteins." Nucleic Acids Research 36: 4381-4389, herein incorporated by reference in its entirety.

In a weak force embodiment, nucleic acid molecule is attached to a substrate at one end and is stretched by various weak forces (e.g., electric force, surface tension, or optical force). In this embodiment, one end of the nucleic acid molecule is first anchored to a surface. For example, the molecule can be attached to a hydrophobic surface (e.g., modified glass) by adsorption. The anchored nucleic acid molecules can be stretched by a receding meniscus, evaporation, or by nitrogen gas flow. See e.g., FIG. 5. Chan, et al. (2006) "A simple DNA stretching method for fluorescence imaging of single DNA molecules." Nucleic Acids Research 34(17): e1-e6, herein incorporated by reference in it entirety.

In the general methods described herein, the nucleic acids can be stretched by a factor of 1.5 times the crystallographic length of the nucleic acid. In another embodiment, the nucleic acid in solution (e.g., has a random-coil structure) is stretched by retracting the meniscus of a solution at a constant rate (e.g., 300 μm/s). Without being bound by a particular theory, the ends of the nucleic acid strands are believed to be frayed (e.g., open and exposing polar groups) that bind to ionisable groups coating a modified substrate (e.g., silanized glass plate) at a pH below the pKa of the ionisable groups (e.g., ensuring they are charged enough to interact with the ends of the nucleic acid molecule). The rest of the nucleic acid molecule (e.g., dsDNA) can not form these interactions. As the meniscus retracts, surface retention creates a force that acts on the nucleic acid molecule to retain it in the liquid phase; however this force is inferior to the strength of the nucleic acid molecule's attachment; the result is that the nucleic acid molecule is stretched as it enters the air phase; as the force acts in the locality of the air/liquid phase, it is invariant to different lengths or conformations of the nucleic acid molecule in solution, so the nucleic acid molecule of any length will be stretched the same as the meniscus retracts. As this stretching is constant along the length of a the nucleic acid molecule, distance along the strand can be related to base content; 1 γm is approximately equivalent to 2 kb.

The pH of the solution used in a receding meniscus method can affect the efficiency of nucleic acid binding to the substrate. On hydrophobic surfaces good binding efficiency can be reached at a pH of approximately 5.5. For example, at pH 5.5, approximately 40-kbp DNA is 10 times more likely to bind by an extremity than by a midsegment. Allemand, et al. (October 1997) "pH-Dependent Specific Binding and Combing of DNA." Biophysical Journal 73: 2064-2070, herein incorporated by reference in its entirety.

Another embodiment, the nucleic acid molecule is stretched by dissolving the nucleic acid molecules in a drop of buffer and running down the sloping substrate very slowly. In a further embodiment, the nucleic acids is embedded in agarose blocks, placed on a substrate. The agarose block comprising the nucleic acid is then melted and dragged along the substrate with a second substrate (e.g., coverslip).

In another embodiment of the invention, comprises reversibly orienting long-chain nucleic acids on hydrophilic substrates without a fluid meniscus. End-tethered nucleic acid mushrooms are elongated by a hydrodynamic flow in the presence of trivalent cations, resulting in electrostatic adsorption of the stretched nucleic acid to the substrate. By complexation of the cations the part of the nucleic acid molecule which is unspecifically bound to the surface desorbs quantitatively, and the mushroom conformation is restored. With the use of multiple deposition-combing steps, combined with a final desorption step, tethering densities higher than attainable with single deposition steps can be obtained. Koota, et al. (Aug. 4, 2007) "Reversible, Meniscus-Free Molecular Combing of Long-Chain DNA" Langmuir 23(18): 9365-9368, herein incorporated by reference in its entirety.

Cleavage Regions

The nucleic acid combed on the substrate can be cleaved into substantially uniform fragments by physical techniques (e.g., shearing, microwave energy, laser, sonicating, microblades, photolytic), chemical techniques (e.g., chemical hydroxyl radical generators), or enzymatic techniques (e.g., nucleases). In one embodiment of the invention, the chemical or enzymatic agents enabling cleavage are associated (covalently or non-covalently) with the patterned cleavage regions. Typically, cleavage regions are in an inactive state during steps of nucleic acid combing or the cleavage regions are created on a surface after nucleic acids are stretched across the surface.

Nucleases

Nucleases suitable for use in the methods described herein include double-stranded nucleases and single-stranded nucleases (e.g., nucleases that preferentially digest single-stranded nucleic acid regions, referred to herein as "single-stranded nucleases.")

The double-stranded nucleases can be non-specific, digesting both RNA and DNA, and/or variants thereof. In other embodiments, the double-stranded nucleases preferentially digest double-stranded RNA, e.g., "double-stranded RNases," or preferentially digest double-stranded DNA, e.g., "double-stranded DNases." Finally, nucleases may be exonucleases that digest only from the 5'-end of a polynucleotide, e.g., 5' double-stranded nucleases, the 3'-end of a polynucleotide, e.g., 3' double-stranded nucleases, or both ends of a double-stranded polynucleotide. Alternatively, endonucleases that cleave at locations within a nucleic acid strand can be used.

The single-stranded nucleases can be non-specific, digesting both RNA and DNA, and/or variants thereof. In other embodiments, the single-stranded nucleases preferentially digest single-stranded RNA, e.g., "single-stranded RNases," or preferentially digest single-stranded DNA, e.g., "single-stranded DNases." Finally, nucleases may digest only from the 5'-end of a polynucleotide, e.g., 5' single-stranded nucleases, the 3'-end of a polynucleotide, e.g., 3' single-stranded nucleases, or both ends of a single-stranded polynucleotide.

In one embodiment, the nuclease digests single-stranded (e.g., unduplexed) nucleic acids and/or single-stranded regions of nucleic acids of nucleic acid molecules and samples. In an alternative embodiment, the nuclease selectively digests the single-stranded nucleic acids of the sample. In yet another embodiment, the nuclease selectively digests the single-stranded nucleic acids of the unbound nucleic acid molecules. The specific nuclease selected for nuclease treatment depends on the desired selectivity (e.g., nucleic acid molecule and/or sample digestion) and nature of the nucleic acids making up the nucleic acid molecule and sample.

RNase A is an example of an RNA nuclease that can be used to remove single-stranded RNA. RNase A effectively recognizes and cuts single-stranded RNA, including RNA in RNA:DNA hybrids that is not in a perfect double-stranded complex. Moreover, RNA bulges, loops, and even single base mismatches can be recognized and cleaved by RNase A. S1 nuclease and Mung Bean nuclease are examples of DNA nucleases with similar properties for single-stranded DNA. Single-stranded nucleases for use in the invention described herein include, but are not limited to, those listed in Table 1.

TABLE 1

Nucleases

| | Nuclease preferentially digests: | Supplier |
|---|---|---|
| Single-stranded nucleases | | |
| S1 nuclease | single-stranded DNA single-stranded RNA | multiple sources[1] |
| Mung-bean nuclease | single-stranded DNA | multiple sources[1] |
| Ribonuclease A | single-stranded RNA | multiple sources[1] |
| RNAse T1 | single-stranded RNA | multiple sources[1] |
| Exonuclease I | Single-stranded DNA 3'→5' | multiple sources[1] |
| RNase ONE ® | single-stranded RNA | Promega Corporation |
| Double-stranded nucleases | | |
| Deoxyribonuclease I (DNAase I) | Single-stranded or double-stranded DNA | multiple sources[1] |
| Nuclease BAL 31 | Single-stranded or double-stranded DNA | multiple sources[1] |
| DNAse II | Double-stranded DNA | multiple sources[1] |
| Exonuclease III | 3' terminal of double-stranded DNA | multiple sources[1] |
| Nuclease BAL 31 | Double-stranded or single-stranded DNA | multiple sources[1] |

[1]Exemplary suppliers: New England Biolabs, Ipswich, MA; Promega Corporation, Madison, WI; and Applied Biosystems, Foster City, CA.

Many nucleases (including the exemplary nucleases of Table I) are well known in the art and are commercially available for use with the invention. These nucleases may be used either alone or in combination. The attributes of nucleases that may make their single or combined use more desirable are well known in the art.

Deoxyribonuclease I (DNAase I) cleaves double-stranded or single stranded DNA. Cleavage preferentially occurs adjacent to pyrimidine (C or T) residues, and the enzyme is therefore an endonuclease. Major products are 5'-phosphorylated di, tri and tetranucleotides. In the presence of magnesium ions, DNase I hydrolyzes each strand of duplex DNA independently, generating random cleavages. In the presence of manganese ions ($Mn^{2+}$), the enzyme cleaves both strands of DNA at approximately the same site, producing blunt ends or fragments with 1-2 base overhangs. DNase I does not cleave RNA, but crude preparations of the enzyme are contaminated with RNase A; RNase-free DNase I is readily available.

Exonuclease III (*E. coli*) removes mononucleotides from the 3' termini of duplex DNA. The preferred substrates are DNAs with blunt or 5' protruding ends. It will also extend nicks in duplex DNA to create single-stranded gaps. It works inefficiently on DNA with 3' protruding ends, and is inactive on single-stranded DNA.

Nuclease BAL 31 (*Alteromonas*) is an exonuclease that digests both 5' and 3' ends of double-stranded DNA. It also acts as a single-stranded endonuclease that cleaves DNA at nicks, gaps and single stranded regions. Nuclease BAL 31 does not cleave internally in duplex DNA.

Ribonuclease T1 (*Aspergillus*) is an endonuclease that cleaves RNA at 3' phosphates of guanine residues, producing nucleic acid molecules having terminal guanosine 3' phosphates.

For example, S1 nuclease degrades single stranded DNA or RNA from the 5'-end. Duplexed DNA, duplexed RNA, and DNA:RNA hybrids are relatively resistant to this enzyme. S1 nuclease is also known to be more active on DNA than RNA. Mung-bean nuclease degrades single-stranded DNA from both ends. Duplexed DNA, duplexed RNA, and DNA:RNA hybrids are relatively resistant to Mung-bean nuclease. Ribonuclease A is an endoribonuclease that specifically digests single-stranded RNA 3' to pyrimidine residues. RNase T1 is an endoribonuelease that specifically attacks the 3' phosphate groups of guanine nucleotides and cleaves the 5'-phosphate linkage to the adjacent nucleotide. Divalent zinc cation ($Zn^{+2}$) is a chemical catalyst that hydrolyzes the phosphodiester bonds of RNA, but not those of DNA. Additionally nucleases are known in the art, e.g., Nuclease Bh1 as described in Desai and Shankar (May 2007) "Single-strand-specific nuclease from *Basidiobolus haptosporus* (Nuclease Bh1)." Scientific Research and Essay 2(5): 139-146, herein incorporated by reference in its entirety.

In a preferred embodiment, the nuclease is Micrococcal nuclease, Exonuclease I, Exonuclease III, Exonuclease VII, Nuclease Bal31, mung bean nuclease, S1 nuclease, recBC nuclease, micrococcal nuclease, deoxyribonuclease I (DNAse I), or DNA pol I (exonuclease II).

General guidance regarding the use of a nuclease, such as the amount of enzyme and buffer required, to achieve digestion of a given amount of single-stranded nucleotide is generally provided by the supplier and known in the art. Furtheiinore, cofactors required for nuclease activity of the enzymes are known as inhibitors and activators of the nuclease activity. Cofactors such as metal ions can be excluded from the enzyme during a nucleic acid combing or stretching step, for example, due to the presence of a metal chelating agent. Additionally or alternatively a reagent that inhibits the nuclease activity can be present during nucleic acid combing or stretching. Following combing or stretching, one or more of the following can be carried out: inhibitors of nuclease activity can be removed, cofactors for nuclease activity can be added, or activators of nuclease activity can be added.

Chemical Hydroxyl Radical Generators

The bound nucleic acid molecule may be cleaved by a chemical hydroxyl radical generators including but not limited to: phthalimide hydroperoxides; 4,7-diphenyl-1,10-phenanthroline copper complex; ferrous EDTA derivatives; hydroxy-salicylidene-ethylendiamine-iron complexes; dinuclear copper(II)$N_4S_4$-donor complex; $[Cu(L^1)_2(Br)](ClO_4)_5$ where $L^1$=5,5'-di(1-(triethylammonio)methyl)-2,2'-dipyridyl cation; or $[Cu(L^2)_2(Br)](ClO_4)_5$ where $L^2$=5,5'-di(1-(tributylammonio)methyl)-2,2'-dipyridyl cation bidentate ligands. At least one or a mixture of chemical hydroxyl radical generators may be bound to at least one cleavage region on the substrate. See An, et al. (2006) "Double-strand DNA cleavage by copper complexes of 2,2'-dipyridyl with electropositive pendants." Dalton Trans. 2066-2071; Saito, et al. (1990) "Phthalimide hydroperoxides as efficient photochemical hydroxyl radical generators. A novel DNA-cleaving agent." J. Am. Chem. Soc. 112(2): 883-884; Quan, et al. (Feb. 14, 2007) "Generation of hydroxyl radical in aqueous solution by microwave energy using activated carbon as catalyst and its potential in removal of persistent organic substances" Journal of Molecular Catalysis A: Chemical 263(1-2): 216-222; Du Tullis, et al. (Jun. 1, 2000) Superior hydrolytic DNA cleavage by a dinuclear copper(II) $N_4S_4$-donor complex compared with a mononuclear $N_2S_2$-donor close analogue." Organic Chemistry Communications 3(6): 307-309; Routier, et al. (1999) DNA cleavage by hydroxy-salicylidene-ethylendiamine-iron complexes Nucleic Acids Research 27(21): 4160-4166, each of which is herein incorporated by reference in its entirety.

Further, a chemical hydroxyl radical generator may be activated by energy (e.g., microwave, laser, light) including but not limited to photolysis of Af-Hydroxy-2-Pyridone. See Adam, et al. (Jan. 2, 2008) "Oxidative DNA Damage in the Photolysis of Af-Hydroxy-2-Pyridone, a Specific Hydroxyl-Radical Source." Photochemistry and Photobiology 70(3): 287-291; U.S. Pat. No. 5,607,924; and Da Ros, et al. (Nov. 1, 2001) DNA-Photocleavage Agents. Current Pharmaceutical Design 7(17): 1781-1821, each of which are herein incorporated by reference in their entirety.

Substrate

A number of substrates (e.g., solid supports) known in the art are suitable for use with the methods of the invention. In one embodiment, the substrate is modified to contain channels, patterns, layers, or other configurations (e.g., patterned substrate). In particular embodiments of the invention, there is a general direct correlation between the size of the pitch or gap separating cleavage regions and the size of the resultant substantially uniform nucleic acid fragment (e.g., a pitch of 100 nm~300 bases, a pitch of 1 μm~3 kilobases, a pitch of 10 μm~30 kilobases). The pitch can be effectively equivalent to the gap in embodiments wherein the width of the cleavage region is relatively narrow.

The pattern can have a pitch or gap from at least about 1, 2, 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1,000 nm. Alternatively or additionally, the pattern can have a pitch or gap less than at least about 1, 2, 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1,000 nm. The pattern can be stripes, swirls, lines, triangles, rectangles, circles, arcs, checks, plaids, diagonals, arrows, squares, or cross-hatches. The pattern can be linear or curved. The pattern can be repeating, non-repeating, or a mixture of two patterns (e.g., lines of different width). In a preferred embodiment the pitch pattern are stripes at least 10, 20, 30, 40, 50, 60, 70, 80, 90, or 100 nm in width.

The pattern can have a pitch or gap from at least about 1, 2, 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1,000 µm. Alternatively or additionally, the pattern can have a pitch or gap less than at least about 1, 2, 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1,000 µm. The pattern can be stripes, swirls, lines, triangles, rectangles, circles, arcs, checks, plaids, diagonals, arrows, squares, or cross-hatches. The pattern can be linear or curved. The pattern can be repeating, non-repeating, or a mixture of two patterns (e.g., lines of different width). In a preferred embodiment the pitch pattern are stripes at least 10, 20, 30, 40, 50, 60, 70, 80, 90, or 100 µm in width.

In a preferred embodiment, the pattern can have a pitch or gap from at least about 10 to 20, 10 to 30, 10 to 40, 10 to 50, 10 to 60, 10 to 70, 10 to 80, 10 to 90, or 10 to 100 µm. In a further embodiment, the pattern can have a pitch or gap from at least about 100 to 200, 100 to 300, 100 to 400, 100 to 500, 100 to 600, 100 to 700, 100 to 800, 100 to 900, or 100 to 1,000 µm. Alternatively, the pattern can have a pitch or gap from at least about 10 to 20, 10 to 30, 10 to 40, 10 to 50, 10 to 60, 10 to 70, 10 to 80, 10 to 90, or 10 to 100 nm. In a further embodiment, the pattern can have a pitch or gap from at least about 100 to 200, 100 to 300, 100 to 400, 100 to 500, 100 to 600, 100 to 700, 100 to 800, 100 to 900, or 100 to 1,000 nm.

In another preferred embodiment, the pattern can have a pitch or gap from at least about 10 nm to 20 µm, 10 nm to 30 µm, 10 nm to 40 µm, 10 nm to 50 µm, 10 nm to 60 µm, 10 nm to 70 µm, 10 nm to 80 µm, 10 nm to 90 µm, or 10 nm to 100 µm. In further preferred embodiment, the pattern can have a pitch or gap from at least about 100 µm to 10 µm, 100 nm to 20 µm, 100 nm to 30 µm, 100 nm to 40 µm, 100 nm to 50 µm, 100 nm to 60 µm, 100 nm to 70 µm, 100 nm to 80 µm, 100 nm to 90 µm, or 100 nm to 100 µm. In a still further embodiment, the pattern can have a pitch or gap from at least about 100 to 200 µm, 100 nm to 300 µm, 100 nm to 400 µm, 100 nm to 500 µm, 100 nm to 600 µm, 100 nm to 700 µm, 100 nm to 800 µm, 100 nm to 900 µm, or 100 nm to 1,000 µm.

In a preferred embodiment, the substrate comprises a modified surface (e.g., silanized). Silanization comprises covering a surface through self-assembly with silane-like molecules. Mica, glass, quartz, and metal oxide surfaces (e.g., $SiO_2$, $TiO_2$, stainless steel) are preferred substrates to be silanized, because they contain hydroxyl groups which attack and displace the alkoxy groups on the silane thus forming a covalent —Si—O—Si— bond. It should be appreciated that any substrate material with hydroxyl groups can be silanizalized. See also U.S. Pat. Nos. 4,833,093; 6,974,762; and WO 83/002669, each of which is herein incorporated by reference in their entirety. Further a simple liquid-phase silanization protocol for coating substrates for molecular combing is described in Labit, et al. (December 2008) BioTechniques® 45(6):649-658, herein incorporated by reference in its entirety. In one embodiment, only part of the substrate is modified. In another embodiment, a portion of the substrate is modified and has a pattern of cleavage regions. See FIG. 3. In another embodiment, nucleic acids can be combed on cetyl-trimethyl ammonium bromide (CTAB)-coated glass surfaces (e.g., uniform and straight on CTAB-coated surfaces.) Zheng, et al. (December 2004) "Combing DNA on CTAB-coated surfaces." Biophysical Chemistry 112(1): 27-33, herein incorporated by reference in its entirety. It should be appreciated that on hydrophobic silanized surfaces, a nucleic acid may be stuck along its full length with a very high density of attachment points. In contrast, when the substrate (e.g., glass) is coated with hydrophobic polymers (e.g., polymethyl-metacrylate (PMMA), polydimethyl-siloxane (PDMS) or polystyrene) the combed nucleic acid only attaches in a few places to the surface. In one embodiment, the pH is lowered to a value of pH<6 (e.g., pH=2, 3, 4, 4.5, 5, 5.5, 5.7) during combing, the tethering can be restricted to only the extremities of the nucleic acid.

Suitable substrates comprise materials including but not limited to borosilicate glass, agarose, sepharose, magnetic beads, polystyrene, polyacrylamide, membranes, silica, semiconductor materials, silicon, organic polymers, ceramic, glass, metal, plastic polycarbonate, polycarbonate, polyethylene, polyethyleneglycol terephthalate, polymethylmethacrylate, polypropylene, polyvinylacetate, polyvinylchloride, polyvinylpyrrolidinone, and soda-lime glass. The substrate body may be in the form of a bead, box, column, cylinder, disc, dish (e.g., glass dish, PETRI dish), fiber, film, filter, microtiter plate (e.g., 96-well microtiter plate), multi-bladed stick, net, pellet, plate, ring, rod, roll, sheet, slide, stick, tray, tube, or vial. The substrate can be a singular discrete body (e.g., a single tube, a single bead), any number of a plurality of substrate bodies (e.g., a rack of 10 tubes, several beads), or combinations thereof (e.g., a tray comprises a plurality of microtiter plates, a column filled with beads, a microtiter plate filed with beads). In a preferred embodiment, the substrate is glass. In another preferred embodiment, the substrate is modified glass, more preferably silanized glass. Conti, et at. (2003) Current Protocols in Cytometry John Wiley & Sons, Inc.

The nucleic acid sample can be immobilized, coated on, bound to, stuck, adhered, or attached to any of the forms of substrates described herein (e.g., bead, box, column, cylinder, disc, dish (e.g., glass dish, PETR1 dish), fiber, film, filter, microtiter plate (e.g., 96-well microtiter plate), multi-bladed stick, net, pellet, plate, ring, rod, roll, sheet, slide, stick, tray, tube, or vial). In particular, particles or beads can be a component of a gelling material or can be separate components such as latex beads made of a variety of synthetic plastics (e.g., polystyrene).

One embodiment of the invention is directed to the use of plates, such as microtiter plates, which support and contain the solid-phase for solid-phase synthetic reactions. In this embodiment, the microtiter plates may house beads that are used as the solid-phase. By "particle" or "microparticle" or "nanoparticle" or "bead" or "microbead" or "microsphere" herein is meant microparticulate matter having any of a variety of shapes or sizes. The shape can be generally spherical but need not be spherical, being, for example, cylindrical or polyhedral. As will be appreciated by those in the art, the particles can comprise a wide variety of materials depending on their use, including, but not limited to, cross-linked starch, dextrans, cellulose, proteins, organic polymers including styrene polymers such as polystyrene and methylstyrene as well as other styrene co-polymers, plastics, glass, ceramics, acrylic polymers, magnetically responsive materials, colloids, thoriasol, carbon graphite, titanium dioxide, nylon, latex, and TEFLON®. See e.g., "Microsphere Detection Guide" from Bangs Laboratories, Fishers, Ind.

The beads need not be spherical; irregular particles may be used. In addition, the beads may be porous, thus increasing the surface area of the bead available for either capture probe attachment or tag attachment. The bead sizes range from nanometers, e.g., 100 nm, to millimeters, e.g., 1 mm, with beads from about 0.2 micron to about 200 microns being preferred, and from about 0.5 to about 5 micron being particularly preferred, although in one embodiment smaller beads may be used.

At least one surface of a substrate can be modified to contain discrete, individual sites for later association of microspheres. These sites may comprise physically altered sites, e.g., physical configurations such as wells or small depressions in the substrate that can retain the beads, such that a microsphere can rest in the well, or the use of other forces (magnetic or compressive), or chemically altered or active sites, such as chemically functionalized sites, electrostatically altered sites, hydrophobically/hydrophilically functionalized sites, or spots of adhesive.

Generally in this embodiment, the microspheres are non-covalently associated in the wells, although the wells may additionally be chemically functionalized as is generally described below, cross-linking agents may be used, or a physical barrier may be used, e.g., a film or membrane over the beads.

In a preferred embodiment, the surface of the substrate is modified to contain chemically modified sites that can be used to attach, either covalently or non-covalently, the microspheres of the invention to the discrete sites or locations on the substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic attachment of the microspheres, e.g., when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites. As outlined above, "pattern" in this sense includes the use of a uniform treatment of the surface to allow attachment of the beads at discrete sites, as well as treatment of the surface resulting in discrete sites. As will be appreciated by those in the art, this may be accomplished in a variety of ways.

In one embodiment, the beads are not associated with a substrate. That is, the beads are in solution or are not distributed on a patterned substrate.

In a preferred embodiment, the compositions of the invention further comprise a population of microspheres. By "population" herein is meant a plurality of beads as outlined above for arrays. Within the population are separate subpopulations, which can be a single microsphere or multiple identical microspheres. That is, in one embodiment, as is more fully outlined below, the array (e.g., substrate) may contain only a single bead for each capture affinity ligand receptor; preferred embodiments utilize a plurality of beads of each type.

In another embodiment of the invention, a substrate/bead pairing is used that allows the association or attachment of the beads at discrete sites on the surface of the substrate, such that the beads do not move during the course of the assay.

In a preferred embodiment, each microsphere comprises an affinity ligand receptor which binds an affinity ligand coupled to a nucleic acid molecule. In a further embodiment, the affinity ligand receptors are bound to a modified region of the substrate. Preferred attachment of the affinity ligand receptors is through covalent means, although even relatively weak interactions (e.g., non-covalent) can be sufficient to attach an affinity ligand receptor to a surface, if there are multiple sites of attachment per each affinity ligand receptor. Thus, for example, electrostatic interactions can be used for attachment, for example by having beads carrying a charge opposite to the bioactive agent. Alternatively, chemical crosslinking may be done as is known in the art.

In one embodiment, the substrate with the bound affinity ligand receptors may be treated (e.g., subject to denaturing or heated conditions) that disrupt the affinity-ligand/affinity-ligand receptor complex to free the bound nucleic acid-affinity ligand complex before, after, or contemporaneously with the cleavage step. The substrate may be washed, dried, prepared, or otherwise treated to be reused in the methods described herein.

In one embodiment, the substantially uniform nucleic acid fragments may be collected by washing, dilution, removal, elution, or centrifugation. The substantially uniform nucleic acid fragments may be washed, precipitated, lyophilized, sequenced, sub-cloned, amplified, gel purified, frozen, or stored. In another embodiment, the substantially uniform nucleic acid fragments linearly stretched on the substrate can be sequenced or visualized via fluoresce in situ on the substrate.

Affinity Ligands

In a preferred embodiment, by using a different modification (e.g., treatment) of the substrate, the extent and nature of the interactions of the nucleic acid with the substrate can be altered. In one embodiment, an affinity ligand (e.g., biotin) bound to one end of the nucleic acid in combination with an affinity ligand receptor bound to the modified region of the substrate (e.g., modified region of the substrate coated with streptavidin) provides another means to attach the end of the nucleic acid to the surface. When the nucleic acid is only attached to the glass at a few positions, overstretching of the nucleic acid is avoided.

In one embodiment, a nucleic acid molecule will comprise an affinity ligand that binds an affinity ligand receptor under the appropriate conditions. In particular, the affinity ligand is attached to the nucleic acid molecule, preferably at one end of the nucleic acid molecule. The affinity ligand is covalently or non-covalently attached to the nucleic acid molecule.

Alternatively, the nucleic acid molecule comprises a nucleotide analog and the affinity ligand is attached to the nucleotide analog. The attached affinity ligand allows for the nucleic acid molecule to be contacted with a substrate comprising an affinity ligand receptor that binds the affinity ligand, thus binding the nucleic acid molecule to the substrate. In particular, a nucleic acid molecule (comprising an affinity ligand)-sample complex (hybrid) is contacted with a substrate comprising an affinity ligand receptor which binds the nucleic acid molecule-sample complex.

Affinity ligands can be incorporated into a target nucleic acid by use of affinity ligand bearing nucleotides and/or primers in an amplification reaction that is used to produce the target nucleic acid in the methods for generating substantially uniform nucleic acid fragments that are set forth herein. Similar methods can be used to introduce affinity ligands into any nucleic acids useful in the methods set forth herein. Exemplary amplification reactions include, but are not limited to polymerase chain reaction, random primer amplification, rolling circle amplification and other methods as described, for example, in U.S. Patent Application Publication No. 2005/0181394 A1, hereby incorporated by reference in its entirety. Affinity ligands can be introduced by photochemical linkage or other chemical techniques as well.

Affinity ligands and affinity ligand receptors are a pair of moieties that bind to each other through covalent or non-covalent interactions. Examples of affinity ligand-affinity ligand receptor partner moieties include but are not limited to biotin-streptavidin, biotin-avidin, receptor-ligand pairs, heterodimerization motif pairs (e.g., complementary leucine zipper motifs, complementary helix-loop-helix motifs), antigen-antibody interactions, polyhistidine (e.g., 6HIS Tag), digoxygenin tags, aptamer-ligand interactions, or multi-component chemical reactions. Further examples of affinity ligand receptors that bind biotin include but are not limited to avidin, streptavidin (SA), neutravidin, a fragment of SA, a fragment of avidin, and a fragment of neutravidin. In a preferred embodiment, the partner moieties are biotin as the affinity ligand with avidin, neutravidin, or streptavidin as the affinity ligand receptor.

In a preferred embodiment, the nucleic acid molecule may be biotinylated (for example using enzymatic incorporate of biotinylated nucleotides, or photoactivated cross-linking of biotin). Biotinylated nucleic acid molecules can then be captured on a streptavidin-coated surface, as is known in the art. Similarly, other hapten-receptor combinations can be used, such as digoxigenin and anti-digoxigenin antibodies. Alternatively, chemical groups can be added in the form of derivatized nucleotides that can then be used to add the nucleic acid molecule to a surface.

Preferred attachments are covalent, although even relatively weak interactions (e.g., non-covalent) can be sufficient to attach a nucleic acid to a surface, if there are multiple sites of attachment per each nucleic acid. Thus, for example, electrostatic interactions can be used for attachment, for example by having beads carrying a charge opposite to the bioactive agent.

Suitable biotin reagents for attaching biotin to a support surface or a support coupler include amine-reactive biotin labeling reagents include but are not limited to sulfo-NHS-biotin, sulfo-NHS-LC-biotin, sulfo-NHS-LC-LC-biotin, sulfo-NHS-SS-biotin, NHS-PEO$_4$-biotin, NHS-biotin, NHS-LC-biotin, NHS-LC-LC-biotin, PFP-biotin, TFP-PEO-biotin, NHS-iminobiotin trifluoroacetamide, sulfhydryl-reactive biotin labeling reagents (e.g., maleimide-PEO$_2$-biotin, biotin-BMCC, PEO-Iodoacetyl biotin, iodoacetyl-LC-biotin, or biotin-HPDP); carboxyl-reactive biotin labeling reagents (e.g., biotin PEO-amine or biotin PEO-LC-amine); carbohydrate-reactive biotin labeling reagents (e.g., biocytin hydrazide, biotin hydrazide, or biotin-LC-hydrazide); and photoreactive biotin labeling reagents (e.g., psoralen-PEO-biotin). In a preferred embodiment, the affinity ligand comprises biotin and is attached to the substrate or substrate coupler using the amine reactive biotin labeling reagent sulfo-NHS-LC-biotin.

Methods similar to those set forth above for attaching affinity ligands, can be used to attach chemically reactive moieties to nucleic acids and to solid support surfaces. The functionalization of solid support surfaces (e.g., substrate) such as certain polymers with chemically reactive groups such as thiols, amines, and carboxyls are generally known in the art. Accordingly, surface chemistries can be used to facilitate the attachment of the desired functionality by the user. Some examples of these surface chemistries for blank microspheres include, but are not limited to, amino groups including aliphatic and aromatic amines, carboxylic acids, aldehydes, amides, chloromethyl groups, hydrazide, hydroxyl groups, sulfonates, and sulfates. Moieties can be added to nucleic acids that are reactive with such surface functionalizations. The moieties can be added, for example, by chemical modification of nucleic acids, or by incorporation of modified primers and/or nucleotides into the amplicon products of an amplification reaction.

Samples

Samples for use in the methods described herein include, but are not limited to, a portion of a gene, a regulatory sequence, genomic DNA, cDNA, and RNA including mRNA and rRNA. The sample may be any length. As will be appreciated by those in the art, the complementary target sequence may take many forms. For example, it may be contained within a larger nucleic acid sequence (e.g., all or part of a gene or mRNA, a restriction fragment of a plasmid or genomic DNA, vector). In particular embodiments, a sample used in a method of the invention is a genome isolated from one or more cells. The sample can be an amplified product obtained from a genome such as the product of a representational amplification method or whole genome amplification method, for example as described in U.S. Patent Application Publication No. 2005/0181394 A1, hereby incorporated by reference in its entirety.

In a preferred embodiment, the sample is a library of clonal nucleic acids, including DNA and RNA. In this embodiment, individual nucleic acids are prepared, generally using conventional methods (including, but not limited to, propagation in plasmid or phage vectors, amplification techniques including PCR). Nucleic acid libraries may be prepared using standard techniques or may be obtained commercially (Life Technologies, Carlsbad, Calif.). Nucleic acid libraries for use in the present invention include those comprising populations of single-stranded or double-stranded nucleic acid molecules, or preferably populations of single-stranded or double-stranded DNA molecules. More preferred nucleic acid libraries to be normalized in accordance with the invention include those comprising complementary DNA (cDNA) libraries. cDNA libraries (double stranded or single stranded) can be made using well known techniques using messenger RNA or polyA+ RNA or may be obtained commercially, for example from Life Technologies (Carlsbad, Calif.), or other commercial sources that will be familiar to one of ordinary skill. cDNA libraries used in accordance with the invention are preferably made with reverse transcriptases having substantially reduced RNase H activity. cDNA libraries are housed in vectors that include, but are not limited to, plasmids, cosmids, and phages. Nucleic acid libraries as described herein can be used as samples in the method described herein.

Nucleic acid samples (including nucleic acid libraries) may be prepared from populations of nucleic acid molecules obtained from natural sources that include, but are not limited to, organdies, cells, tissues, organs, or organisms. Cells that may be used as sources of nucleic acid molecules may be prokaryotic (bacterial cells, e.g., *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacte-*

*rium, Helicobacter, Erwinia, Agrobacterium, Rhizobium*, and *Streptomyces* genera); archeaon, such as crenarchaeota, nanoarchaeota or euryarchaeotia; or eukaryotic such as fungi, (e.g., yeasts), plants, protozoans and other parasites, and animals (including insects (e.g., *Drosophila* spp.), nematodes (e.g., *Caenorhabditis elegans*), and mammals (e.g., rat, guine pig, horse, tapir, cow, sheep, goat, mouse, monkey, non-human primate and human)).

Mammalian somatic cells that may be used as sources of samples (including libraries) of nucleic acids include blood cells (e.g., reticulocytes and leukocytes), endothelial cells, epithelial cells, neuronal cells (e.g., from the central or peripheral nervous systems), muscle cells (e.g., myocytes and myoblasts from skeletal, smooth or cardiac muscle), connective tissue cells (e.g., fibroblasts, adipocytes, chondrocytes, chondroblasts, osteocytes and osteoblasts) and other stromal cells (e.g., macrophages, dendritic cells, Schwann cells). Mammalian germ cells (e.g., spermatocytes and oocytes) may also be used as sources of nucleic acids or libraries for use in the invention, as may the progenitors, precursors and stem cells that give rise to the above somatic and germ cells. Also suitable for use as nucleic acid sources are mammalian tissues or organs such as those derived from brain, kidney, liver, pancreas, blood, bone marrow, muscle, nervous, skin, spinal cord, genitourinary, circulatory, lymphoid, gastrointestinal and connective tissue sources, as well as those derived from a mammalian (e.g., mouse, rat, hamster, horse, cow, sheep, goat, pig, monkey, human) embryo, or fetus.

Any of the above prokaryotic or eukaryotic cells, tissues and organs may be normal, diseased, transformed, established, progenitors, precursors, fetal or embryonic. Diseased cells include those involved in infectious diseases (caused by bacteria, fungi or yeast, viruses, or parasites), in genetic or biochemical pathologies (e.g., cystic fibrosis, hemophilia, Alzheimer's disease, Huntington's disease, Parkinson's Disease, muscular dystrophy or multiple sclerosis) or in cancerous processes. Transformed or established animal cell lines (e.g., 293-T cells, 3T3 cells, 721 cells, 9L cells, A172 cells, A20 cells, A253 cells, A2780 cells, A431 cells, A-549 cells, ALC cells, B16 cells, B35 cells, Bas8 cells, BCP-1 cells, BHK cells, BHK-21 cells, BR 293 cells, BxPC3 cells, C3H-10T1/2 cells, C6 cells, C6/36 cells, Cal-27 cells, CHL-60 cells, CHO cells, CMLT1 cells, CMT cells, COR-L23 cells, COS cells, CT26 cells, D17 cells, DH82 cells, DU145 cells, EL4 cells, EM2 cells, EM3 cells, F9 cells, FM3 cells, H1299 cells, H69 cells, HB54 cells, HB55 cells, HCA2 cells, HEK-293 cells, HeLa cells, Hepalcic7 cells, HepG2 cells, HMEC cells, HT-29 cells, Jurkat cells, JY cells, K562 cells, KCL22 cells, KG1 cells, Ku812 cells, KYO1 cells, Lncap cells, MC-38 cells, MCF-10A cells, MCF-7 cells, MDA-231 cells, MDA-468 cells, MDA-MB-438 cells, MDCK II cells, N6 cells, NALM-1 cells, NIH-3T3 cells, NW-145 cells, PC3 cells, PC12 cells, RenCa cells, Saos-2 cells, Sf9 cells, Sf21 cells, SHSY5Y cells, T47D cells, T84 cells, THP-1 cells, U373 cells, U87 cells, U937 cells, VERO cells, WM39 cells, X63 cells, YAC-1 cells, YAR cells) can be used as the source of nucleic acid sample material for use in the present invention. Other cells, cell lines, tissues, organs and organisms suitable as sources of nucleic acids for use in the present invention will be apparent to one of ordinary skill in the art. These cells, tissues, organs and organisms may be obtained from their natural sources, or may be obtained commercially from sources such as American Type Culture Collection (Rockville, Md.) and others that are known in the art.

Once the starting cells, tissues, organs or other samples are obtained, nucleic acid molecules (e.g., mRNA or poly A+ RNA) can be isolated, and nucleic acid libraries (e.g., cDNA libraries) prepared therefrom, by methods that are well-known in the art. See, e.g., Maniatis, et al. (1978) Cell 15:687-701; Okayama and Berg (1982) Mol. Cell. Biol. 2:161-170; Gubler and Hoffman (1983) Gene 25:263-269, the disclosures of each of which are herein incorporated by reference in their entireties. Nucleic acid libraries prepared in such a manner will typically contain a vast range of abundances of member nucleic acid molecules, depending upon the cell, tissue or organism source, and the stage of development or cell cycle of the source.

A sample useful in the methods set forth herein, can be an isolated genome from a cell or organism such as one of those set forth above. A genome useful in the methods can be a substantially complete genome or fraction thereof. For example, the sample can include a complexity of at least 80%, 90%, 95%, 99% or 99.9% of an organism's genome. Less complex samples can be used as well including for example, a sample having no more than 50%, 40%, 30%, 20% 10%, 5% or 1% of an organism's genome.

A sample useful in the methods described herein can be a nucleic acid library including but not limited to a genomic DNA library, cDNA library, eukaryotic DNA library, Achaean DNA library, or prokaryotic DNA library. The DNA library can have a complexity of at least about 0.5 Gbases, 1 Gbases, 2 Gbases, 3 Gbases, 4 Gbases, 5 Gbases, 10 Gbases or more.

A sample useful in the methods described herein can be a genome, transcriptome, or metagenome.

Nucleic Acid Fragments

Nucleic acid fragments (e.g., oligonucleotides) produced by the methods as described herein comprise at least two nucleotides. In particular embodiments, the nucleic acid fragments can be at least about 10, 25, 50, 100, 150, 200, 250, 300, 350, 400, 450, 500, 550, 600, 650, 700, 750, 800, 850, 900, 950 or 1000 bases. Alternatively or additionally, the nucleic acid fragments (e.g., oligonucleotides) can be of a length that is no more than 1000, 900, 800, 700, 600, 500, 400, 300, 200, 150, 100, 75, 50, 25 or 10 nucleotides (e.g., base pairs) or shorter. In another embodiment, the nucleic acid fragments can be at least 1, 2, 3, 4, 5, 6, 7, 8, 9, or 10 kb, as well as about 10, 11, 12, 13, 14, 15, 16, 17, 18, 19, or 20 kb, as well as about 10, 20, 25, 30, 35, 40, 45, 50, 55, 60, 65, 70, 75, 80, 85, 90, 95 or 100 kb, as well as about 100, 200, 300, 400, 500, 600, 700, 800, 900, or 1,000 Kb and all increments therein.

In particular embodiments, the nucleic acid fragments can be at least about 1, 2, 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1,000 bases in length. The nucleic acid fragments can be at least about 1, 2, 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, or 1,000 kb in length. In a preferred embodiment, the nucleic acid fragment can be about at least 10, 20, 30, 40, 50, 60, 70, 80, 90, or 100 kb in length.

In a preferred embodiment, the nucleic acid fragments can be from at least about 10 to 20, 10 to 30, 10 to 40, 10 to 50, 10 to 60, 10 to 70, 10 to 80, 10 to 90, or 10 to 100 basesin length. In a further embodiment, the nucleic acid fragments can be at least about 100 to 200, 100 to 300, 100 to 400, 100 to 500, 100 to 600, 100 to 700, 100 to 800, 100 to 900, or 100 to 1,000 basesin length. Alternatively, the nucleic acid fragments can be at least about 10 to 20, to 30, 10 to 40, 10 to 50, 10 to 60, 10 to 70, 10 to 80, 10 to 90, or 10 to 100 kb. In a further embodiment, the nucleic acid fragments can be at least about 100 to 200, 100 to 300, 100 to 400, 100 to 500, 100 to 600, 100 to 700, 100 to 800, 100 to 900, or 100 to 1,000 kb.

Nucleic acid fragments produced by the methods as described herein may be single stranded or double stranded, as specified, or contain portions of both double stranded and single stranded sequence. The nucleic acid fragments may be DNA, both genomic and cDNA, RNA or a hybrid, where the nucleic acid fragments comprise any combination of deoxyribo- and ribo-nucleotides, and any combination of bases, including uracil, adenine, thymine, cytosine, guanine, inosine, xanthanine, hypoxanthanine, isocytosine, isoguanine, and base analogs such as nitropyrrole and nitroindole.

The nucleic acid sample can be contacted with the substrate prior to, subsequent to, or simultaneously with contacting the cleavage region. Alternatively, the nucleic acid sample can be contacted with the substrate prior to cleaving the nucleic acid sample.

Automation

The methods described herein can be performed (or optimized) for use in automated systems. In particular, the methods described herein are suitable for use with robot, computerized, and/or automated systems.

It is advantageous that at least some manipulations needed by the methods described herein may be assisted or performed automatically. In view of the exemplary methods described herein, an automated apparatus for the generation of substantially uniform nucleic acid fragments advantageously includes facilities for handling fluids, for manipulating reaction vessels, and for storage of reagents and building blocks. Advantageous facilities for fluid handling include: facilities to accurately dispense solutions and slurries which contain building blocks, solid-phase substrates, reagents, and/or solvents into the reaction vessels; facilities to rapidly and repetitively add wash solvents into the reaction vessels; and facilities to rapidly and accurately remove fluid phases from the reaction vessels leaving behind the solid-phase supports within the reaction vessels with respective attached intermediate compounds. Facilities for manipulating reaction vessels and reaction vessel arrays include: facilities to move reaction vessels and reaction vessel arrays between various stations; facilities for time and temperature controlled incubation of reaction vessels and reaction vessel arrays; and optionally facilities for agitation of reaction vessels during incubation. Each such protocol typically uses many building blocks, perhaps hundreds, a several activating and other reagents, and one or two work solvents.

Suitable apparatuses for use with the invention advantageously permit simultaneous, parallel processing to occur during solid-phase synthesis in order to achieve high synthesis throughput. This is achieved because the design of the apparatus includes a few standardized physical sizes and layouts having a modular nature. Further, suitable apparatuses may comprise a Programmable Logic Controller (PLC). Therefore, processing resources can be simultaneously applied to multiple protocols in many reaction vessels which can be sized to achieve high throughput.

Preferred materials for all elements of the invention in contact with the synthetic addition reactions, in particular the reaction vessels, typically resist the harsh reagents, solvents, and reaction conditions likely to be encountered in the various protocols. In the following detailed description, when solvent resistance is specified and particular materials are not specified, the following exemplary general purpose solvent resistant materials can be used: TEFLON®, plastics (e.g., polypropylene) or glass.

A variety of different control mechanisms are used in the methods (reactions) in accordance with the present invention. The present invention is adaptable to controls requiring manual intervention for some, or even all, processing steps of generation of substantially uniform nucleic acid fragments. The apparatus of the invention is also adaptable to semi-automatic or fully-automatic controllers. Automatic control mechanisms should be sufficiently general that a different reaction can occur in each reaction vessel, substrate or fluidic device of each array of wells utilized by the apparatus, and that a different substantially uniform nucleic acid fragment sample can be obtained. Finally, the automatic controller should be able to manage a plurality of substrates, fluidic devices, fluid dispensers, rotor assemblies, and other work stations and subassemblies such that all components of the apparatus are optimally engaged or performing tasks for the reactions and steps set forth herein.

The automatic control mechanisms are supported by certain hardware and software elements. General hardware elements preferably include one or more general control computers, an optional number of specialized control processors, and electrical interfaces to all controlled components of the apparatus (e.g., Programmable Logic Controller). In a manner known in the art, all the directly and indirectly controlled components of the apparatus can be provided with electrical interfaces having certain standardized electrical characteristics. Certain of these low-level hardware interfaces are directly linked from their standardized interfaces to interfaces of the general control computers. Optionally, for complex resources, such as complex work stations, an intermediate level of specialized control processors is interposed between the general control computers and the low-level electrical interfaces of such resources.

The general control computers can be sufficiently capable personal computers (PC's) provided with such specialized electrical interfaces. An exemplary personal computer includes an Intel PENTIUM® processors running at 1.0, 2.0, or 3.0 GHz with a 1, 5, 10 gigabyte or greater hard drive, 10 gigabytes or more of memory, and commercially available interface boards providing interfaces such as D/A or on/off output circuits or links to standard instrument control buses (e.g., Intel PENTIUM® D 3.2 GHz Duel Core processor). Specialized CPU's on custom PC boards for valve control, for example, an INTEL® 8051 compatible microprocessor, or other commercial motion control systems, for example, a COMPUMOTOR® 6K2, can be for low level control in accordance with the present invention. A PC running LINUX® and a custom designed control application (high level control) can be used to communicate with and control the low level controllers via Ethernet and serial (e.g., RS-232) lines in accordance with the present invention. One should appreciate that such hardware control elements can be directly accessed or indirectly accessed via suitable internet or intranet connection.

General software elements executed by the general control computers include operating system software, low-level moment-to-moment control and monitoring software, scheduling and monitoring software, and synthesis planning software. At the lowest software level is the operating system software of the general control computers, which in an exemplary embodiment, can be UNIX® or WINDOWS XP® (Microsoft Corporation).

Array Methods

Nucleic acid fragments produced in a method set forth herein can be analyzed or evaluated using microarray methods. As used herein, the term "microarray" refers to a population of different probe molecules that are attached to one or more substrates such that the different probe molecules can be differentiated from each other according to relative location. An array can include different probe molecules, or populations of the probe molecules, that are each located at a different addressable location on a substrate. Alternatively, a microarray can include separate substrates each bearing a different probe molecule, or population of the probe molecules, that can be identified according to the locations of the substrates on a surface to which the substrates are attached or according to the locations of the substrates in a liquid. Exemplary arrays in which separate substrates are located on a surface include, without limitation, a Sentrix® Array or Sentrix® BeadChip Array available from Illumina®, Inc. (San Diego, Calif.) or others including beads in wells such as those described in U.S. Pat. Nos. 6,266,459, 6,355,431, 6,770,441; and 6,859,570; and PCT Publication No. WO 00/63437, each of which is hereby incorporated by reference. Other arrays having particles on a surface include those set forth in U.S. Patent Application Publication No. 2005/0227252; WO 05/033681; and WO 04/024328. Nucleic acid fragments can be bound to specific probes at separate features of an array for individual detection and analysis of particular species of nucleic acid fragments. Typically probes are nucleic acid molecules having sequences that are complementary to sequences in target nucleic acid fragments. However, other probes can be used if desired.

Further examples of commercially available microarrays that can be used in the invention include, for example, an Affymetrix® GeneChip® microarray or other microarray synthesized in accordance with techniques sometimes referred to as VLSIPS™ (Very Large Scale Immobilized Polymer Synthesis) technologies as described, for example, in U.S. Pat. Nos. 5,324,633; 5,744,305; 5,451,683; 5,482,867; 5,491,074; 5,624,711; 5,795,716; 5,831,070; 5,856,101; 5,858,659; 5,874,219; 5,968,740; 5,974,164; 5,981,185; 5,981,956; 6,025,601; 6,033,860; 6,090,555; 6,136,269; 6,022,963; 6,083,697; 6,291,183; 6,309,831; 6,416,949; 6,428,752; and 6,482,591, each of which is hereby incorporated by reference. A spotted microarray can also be used in a method of the invention. An exemplary spotted microarray is a CodeLink™ Array available from Amersham Biosciences. Another microarray that is useful in the invention is one that is manufactured using inkjet printing methods such as SurePrint™ Technology available from Agilent Technologies. Other microarrays that can be used in the invention include, without limitation, those described in Butte, *Nature Reviews Drug Discov.* 1:951-60 (2002) or U.S. Pat. Nos. 5,429,807; 5,436,327; 5,561,071; 5,583,211; 5,658,734; 5,837,858; 5,919,523; 6,287,768; 6,287,776; 6,288,220; 6,297,006; 6,291,193; and 6,514,751; WO 93/17126; and WO 95/35505, each of which is hereby incorporated by reference.

Neighboring features of an array can be discrete, one from the other, in that they do not overlap. Accordingly, the features can be adjacent to each other or separated by a gap. In embodiments where features are spaced apart, neighboring sites can be separated, for example, by a distance of less than 100 µm, 50 µm, 10 µm, 5 µm, 0.5 µm, or less. The layout of features on an array can also be understood in terms of center-to-center distances between neighboring features. An array useful in the invention can have neighboring features with pitch (for example, measured as center-to-center spacing) of less than about 100 µm, 50 µm, 10 µm, 5 µm, 1 µm, 0.5 µm, or less. Furthermore, it will be understood that the distance values described above and elsewhere herein can represent an average distance between neighboring features of an array. As such, not all neighboring features need to fall in the specified range unless specifically indicated to the contrary, for example, by a specific statement that the distance constitutes a threshold distance between all neighboring features of an array.

The methods set forth herein can be used to make arrays having features at any of a variety of densities. Very high density arrays are useful in the invention including, for example, those having at least about 10,000,000 features/$cm^2$, at least about 100,000,000 features/$cm^2$ or at least about 1,000,000,000 features/$cm^2$. High density arrays include, for example, those having at least about 100,000 features/$cm^2$, at least about 1,000,000 features/$cm^2$ or at least about 5,000,000 features/$cm^2$ up to about 10,000,000 features/$cm^2$ Moderate density arrays can have at least about 10,000 features/$cm^2$, at least about 20,000 features/$cm^2$ or at least about 50,000 features/$cm^2$ up to about 100,000 features/$cm^2$. Low density arrays are generally less than 10,000 features/$cm^2$ with from about 1,000 features/$cm^2$ to about 5,000 features/$cm^2$ or 10,000 features/$cm^2$ being useful in particular embodiments. Very low density arrays having less than 1,000 features/$cm^2$, from about 10 features/$cm^2$ to about 1,000 features/$cm^2$, or from about 100 features/$cm^2$ to about 500 features/$cm^2$ are also useful in some applications.

A surface used in the invention, whether as a cleavage device or an analytical device such as an array, may be contained in a flow chamber allowing convenient movement of liquids across the surface to enable the transfer of reagents. Exemplary flow cells that can be used are described in WO 2007/123744, hereby incorporated by reference in its entirety.

Arrays that have been fabricated using beads are particularly useful for multiplex detection of nucleic acids due to the high density of probes present on the arrays. The presence or quantity of particular sequences in a sample can be determined, for example, based on hybridization specificity between the particular sequences and the affinity ligand receptor present on an array. If desired, bound samples can be amplified prior to being contacted with an array, for example, using PCR methods, rolling circle amplification methods, random prime amplification methods or the like, in order to prepare copies of target sample (e.g., nucleic acids).

Sequencing Methods

The invention also encompasses methods of sequencing of the substantially uniform nucleic acid fragments as prepared by the methods set forth herein. In one embodiment, the methods described herein may be used to prepare size fragments for paired end sequencing libraries of short insert (~300 bases~100 nm pitch), long insert (~3 kb~1 µm pitch), and ultralong insert (~30 kb ~10 µm pitch). The nucleic acid sequencing methods described herein can be automated.

Sequencing can be carried out using any suitable sequencing technique including, for example, sequencing by synthesis techniques wherein nucleotides are added successively to a free 3' hydroxyl group, resulting in synthesis of a nucleic acid chain in the 5' to 3' direction. The nature of the nucleotide added is preferably determined after each nucleotide addition. Sequencing techniques using sequencing by ligation, wherein not every contiguous base is sequenced, and techniques such as massively parallel signature sequencing (MPSS) where bases are removed from, rather than added to the strands on the surface are also useful, as are techniques using detection of pyrophosphate release (pyrosequencing).

The initiation point for a sequencing reaction may be provided by annealing of a sequencing primer to a target nucleic acid present at a feature of an array. In this connection, a known adapter region that is present on a target nucleic acid, for example, a target nucleic acid from a cleavage reaction described previously herein, can be used as a priming site for annealing of a sequencing primer.

In a particular embodiment, a nucleic acid sequencing reaction can include steps of hybridising a sequencing primer to a single-stranded region of a linearised nucleic acid fragment (or amplification product thereof) that acts as a sequencing template, sequentially incorporating one or more nucleotides into a nucleic acid strand complementary to the region of the template strand to be sequenced, identifying the base present in one or more of the incorporated nucleotide(s) and thereby determining the sequence of a region of the template strand.

One preferred sequencing method which can be used in accordance with the invention relies on the use of modified nucleotides having removable 3' blocks, for example, as described in WO 04/018497 and U.S. Pat. No. 7,057,026, the contents of which are incorporated herein by reference. Once the modified nucleotide has been incorporated into the growing nucleic acid chain complementary to the region of the template being sequenced there is no free 3'-OH group available to direct further sequence extension and therefore the polymerase can not add further nucleotides. This allows convenient detection of single nucleotide incorporation events. Once the identity of the base incorporated into the growing chain has been determined, the 3' block may be removed to allow addition of the next successive nucleotide. By ordering the products derived using these modified nucleotides, it is possible to deduce the DNA sequence of the DNA template. Multiple reactions can be done in parallel on a single array, for example, if each of the modified nucleotides has a different label attached thereto, known to correspond to the particular base, thereby facilitating discrimination between the bases added during each incorporation step. If desired, a separate reaction may be carried out for each of the modified nucleotides.

Modified nucleotides used in an amplification or sequencing reaction may carry a label to facilitate their detection. A fluorescent label, for example, may be used for detection of modified nucleotides. Each nucleotide type may thus carry a different fluorescent label, for example, as described in U.S. Provisional Application No. 60/801,270 (Novel dyes and the use of their labeled conjugates), published as WO 07/135, 368, the contents of which are incorporated herein by reference. The detectable label need not, however, be a fluorescent label. Any label can be used which allows the detection of an incorporated nucleotide. Similarly, fluorescent labels or other labels can be used to detect any of a variety of analytes on an array fabricated using a bead-based transfer method set forth herein.

One method for detecting fluorescently labeled nucleotides comprises using laser light of a wavelength specific for the labeled nucleotides, or the use of other suitable sources of illumination. The fluorescence from the label on the nucleotide may be detected by a CCD camera or other suitable detection means. Suitable instrumentation for recording images of clustered arrays is described in U.S. Provisional Patent Application No. 60/788,248 (Systems and devices for sequence by synthesis analysis), published as WO 07/123, 744, the contents of which are incorporated herein by reference. Detectors that are capable of obtaining an image of an array surface such as those configured to scan an array surface. Such detectors can be configured to take a static image of an array surface, scan a point across an array surface or scan a line across an array surface. Exemplary scanning devices that can be used are described, for example, in U.S. Pat. No. 7,329,860, which is incorporated herein by reference. A detector can be configured to obtain an image of an array at high resolution, for example, in the low micron to submicron range. In particular embodiments, an image can be obtained at a Rayleigh resolution between 0.2 and 10 micrometers.

The invention is not intended to be limited to use of the sequencing method outlined above, as a variety of sequencing methodologies which utilize successive incorporation of nucleotides into a nucleic acid chain or removal of nucleotides from a nucleic acid chain can be used. Suitable alternative techniques include, for example, Pyrosequencing, FISSEQ (fluorescent in situ sequencing), MPSS and sequencing by ligation-based methods, for example as described is U.S. Pat. No. 6,306,597. Sequencing by hybridization methods can also be used.

A nucleic acid may be analysed to obtain a first and then a second sequencing read from opposite ends of the nucleic acid. Methodology for sequencing both ends of nucleic acids at array features (also referred to as "clusters") are described in co-pending applications WO 07/010,252 and WO 08/041, 002, the contents of which are incorporated by reference herein in their entirety. These methods utilize a step of copying a first nucleic acid fragment (or amplicon thereof) by hybridising the 3' end of this template strand to an immobilised primer followed by extending the resulting bridged structure to generate a second template strand. This copying step can be carried out after the template has been sequenced from a first end. Then the first strand can be cleaved from the surface and the remaining second template strand can be sequenced from the other end. In order to practice this version of the invention, two or more immobilised primers are utilized, at least one of which is configured to be cleavable in order to release the first template strand.

Sequencing can be carried out using other sequencing techniques as well including but not limited to Maxam-Gilbert method, Ladder-based sequencing methods, multiplex sequencing, and sequencing by hybridization. See e.g., U.S. Pat. Nos. 5,674,473; 6,296,810; 7,179,602; 7,272,507; Maxam and Gilbert (1977) Proc. Natl. Acad. Sci. USA 74:560; Church and Kieffer-Higgins (1988) Science 240: 185-188, each of which is hereby incorporated by reference in their entirety.

Suitable sequencing methods also include a nano method of sequencing as described in Lagerqvist, et al. (2006) "Fast DNA Sequencing via Transverse Electronic Transport." Nano Letters 6(4): 779-782, herein incorporated by reference in its entirety. See also Mardis (September 2008) "Next-Generation DNA Sequencing Methods" Annual Review of Genomics and Human Genetics 9: 387-402, herein incorporated by reference in its entirety.

Sequencing methods are preferably carried out with the target polynucleotide arrayed on a solid support as exemplified above in regard to sequencing by synthesis methods. Multiple target polynucleotides can be immobilized on the solid support through linker molecules, or can be attached to particles, e.g., microspheres, which can also be attached to a solid support material.

Sequencing methods can be carried out on both single polynucleotide molecule and multi-polynucleotide molecule arrays, e.g., arrays of distinct individual polynucleotide molecules and arrays of distinct regions comprising multiple copies of one individual polynucleotide molecule. Single molecule arrays allow each individual polynucleotide to be resolved separately. The use of single molecule arrays is preferred. Sequencing single molecule arrays non-destructively allows a spatially addressable array to be formed. Brenner, et al. (2000) "Gene Expression Analysis by Massively Parallel Signature Sequencing (MPSS) on Microbead Arrays." Nature Biotechnology 18:630-634; Drmanac, et al., (1992) "Sequencing by Hybridization (SBH) with Oligonucleotide Probes as an Integral Approach for the Analysis of Complex Genomes." International Journal of Genome Research, 1(1):59-79, each of which is herein incorporated by reference in their entirety. An additional technique utilizes sequencing by hybridization. For example, sequencing by hybridization has been described. Drmanac, et al. (1989) Genomics 4:114; Koster, et al. (1996) Nature Biotechnology 14: 1123; U.S. Pat. Nos. 5,525,464; 5,202,231; and 5,695,940, each of which is hereby incorporated by reference in their entirety. See also Ronaghi, et al., (1998) "A Sequencing Method Based on Real-Time Pyrophosphate." Science 281: 363-365; Syvanen (1999) "From gels to chips: Minisequencing' Primer Extension for Analysis of Point Mutations and Single Nucleotide Polymorphisms." Human Mutation 13:1-10, each of which is herein incorporated by reference in its entirety.

The above description of various illustrated embodiments of the invention is not intended to be exhaustive or to limit the invention to the precise disclosed. While specific embodiments of, and examples for, the invention are described herein for illustrative purposes, various equivalent modifications are possible within the scope of the invention, as those skilled in the relevant art will recognize. The invention may be practiced in ways other than those particularly described in the foregoing description and examples. The teachings provided herein of the invention can be applied to other purposes, other than the examples described below.

Certain teachings related to methods for the generation of uniform fragments of nucleic acids using patterned substrates were disclosed in U.S. Provisional patent application No. 61/166,356, filed Apr. 3, 2009, the disclosure of which is herein incorporated by reference in its entirety.

The entire disclosure of each document cited (including patents, patent applications, journal articles, abstracts, manuals, books, or other disclosures) in the Background of the Invention, Detailed Description, and Examples is herein incorporated by reference in their entireties.

EXAMPLES

The examples contained herein are offered by way of illustration and are not intended to limit the invention.

Example 1

Silanization Protocol

A protocol (e.g., method) for the production of silanized substrate (e.g., glass):

1. Clean glass substrates by rinsing with ddH$_2$O before using. The silane tray should then be rinsed with 95% EtOH, and the acetone tray should be rinsed with acetone.
2. Sonicate the substrates in acetone for 10 minutes.
3. After the acetone sonication, wash substrates in ddH$_2$O tray at least twice.
4. Sonicate the substrates in 0.1M NaOH for 10 minutes.

While the substrates are sonicating in NaOH, make the following silane solution under a hood:

TABLE II

| SILANE SOLUTION | | |
|---|---|---|
| REAGENTS | For small trays (30 slides) add: | For large trays (60 slides) add: |
| 95% EtOH | 350 mL | 800 mL |
| Glacial Acetic Acid | 42 µL | 96 µL |
| Glycidoxypropyltrimethoxy silane | 11 mL | 25 mL |

NOTE:
Do not add the silane until the NaOH sonication is finished. After the silane is added, stir for 1-2 minutes.

After the NaOH sonication, the substrates are washed in ddH$_2$O tray at least twice. The substrates are sonicated in silane solution for at least 3 minutes to a recommended maximum of 5 minutes. The substrates are washed in 100% EtOH tray. Then dried in prepurified N$_2$ gas, and stored in 100° C. oven at least 2 hours before using substrates.

2× Phosphate Printing Buffer (pH 10.5)
400 mM Na$_2$HPO$_4$
1.6 M NaCl
NaOH to pH 10.5
Filter Sterilized 1-2000
Add 5 µL to printing plates and 5µL of cDNA to make a 1× working buffer.

Example 2

Preparation of Substrate (e.g., Glass Coverslips)

Fisher premium coverslips (22×30 mm) are sonicated in 2% MICRO-90 soap (Cole-Parmer, Vernon Hills, Ill.) for 20 min and then cleaned by boiling in RCA solution (6:4:1 high-purity H$_2$O/30% NH$_4$OH/30% H$_2$O$_2$) for 1 h. Poly(allylamine) (PAll) and Poly(acrylic acid) (PAcr) (Sigma-Aldrich, St Louis, Mo.) are dissolved at 2 mg/ml in high-purity water. The solutions are adjusted to pH 8.0 using either HCl (for PAll) or NaOH (for PAcr). The polyelectrolyte solutions are then passed through a 0.22 µm filter. The RCA-cleaned coverslips are immersed in the positive (+, PAll) and the negative (−, PAcr) polyelectrolytes according to the scheme +/wash/−/wash/+/wash. Each polyelectrolyte is incubated for 30 min on a shaker at 150 r.p.m. at room temperature (e.g., 25° C.); each wash step comprises at least three rinses with high-purity water. The polyelectrolyte-coated coverslips can be stored in high-purity water at room temperature. See Chan, et al. (2006) "A simple DNA stretching method for fluorescence imaging of single DNA molecules." Nucleic Acids Research 34(17): e1-e6, herein incorporated by reference in it entirety.

Example 3

Preparation of Substrate (e.g., Highly Oriented Pyrolitic Graphite (HOPG))

HOPG nanosheets (e.g., 3.5 to 100 nm thick) can be made as described by Rose, et al. (2006) "Adsorption and Combing of DNA on HOPG Surfaces of Bulk Crystals and Nanosheets: Application to the Bridging of DNA between HOPG/Si Hetero-structures." Nanotechnology 17: 3325 and Martin, et al. (2006) "FIB—created HOPG/SiO$_2$ heterostructures for adsorbed and suspended DNA." IEEE Technical Digest of International Conference on Microtechnologies in Medicine and Biology (MMB2006) page 173, each of which is incorporated by reference in their entirety.

HOPG nanosheets (e.g., 3.5 to 100 nm thick) are made by rubbing a HOPG crystal onto a silicon oxide surface. This substrate can then be patterned with a focused ion beam (FIB) to fabricate HOPG/Si heterostructures (e.g., arrays of silicon micropillars and microtracks decorated on their top surface with HOPG nanosheets). The surface reactivity toward nucleic acids of HOPG nanosheets is the same as of HOPG bulk crystals. Additionally, molecular combing techniques can be used to attach and suspend bundles of approximately 20-50 nucleic acid molecules between HOPG/Si heterostructures.

Example 4

DNA Combing Protocol

In one embodiment of the invention, the combing process comprises stretching of the DNA by the passage of an air/water meniscus. A hydrophobic surface is dipped into a DNA solution (DNA concentration 6.5 pM) at pH 5.5 for silanated surfaces and pH 6.6 for PMMA surfaces. DNA will absorb onto this hydrophobic surface by one extremity in a "mushroom" state. Therefore the adsorbed DNA will have only one attachment point with the surface and will retain its fluctuating coil conformation. The reason the DNA binds to the hydrophobic surface is still a matter of discussion. Without being bound by a specific theory, one explanation relies on pH-induced denaturation of the DNA ends, which then expose the hydrophobic part of bases and thus strongly interact with the surface. Whatever its origin, it should be mentioned that this interaction is very strong, so the DNA can be considered as grafted onto the surface. When the slide is pulled out of the solution the anchored DNA molecules pass through the air/water interface. There, capillary forces pull down the DNA perpendicularly to the meniscus. Because once in contact with air DNA sticks onto the surface, there is no retraction of the molecules, which remain stretched onto the surface once out of the solution. To vary the magnitude of the capillary forces, the combing process is performed under two different conditions: first, with the normal air/water surface tension, and second, with a lower surface tension obtained by spreading a monolayer of fatty alcohol at the air/water interface.

For combing in the presence of fatty alcohol, a droplet of 1-dodecanol is added at the air/water interface just before pulling out the cover slide. Because of the low solubility of 1-dodecanol in water (1 ppm), this addition of alcohol does not interfere with the DNA molecules or glass surface in solution. The presence of a reservoir at the surface maintains the dodecanol monolayer in a dense phase. After the combing process the fatty alcohol is adsorbed on the cover slide during the retraction and is spontaneously evaporated. A motorized translation stage may be used where the substrates are pulled out of the solution at a constant speed (200 m/s). In another embodiment, the speed is 100, 200, 300, 400, 500, 600, 700, 800, 900, or 1,000 μm/s. Gueroui, et al. (Apr. 30, 2002) "Observation by fluorescence microscopy of transcription on single combed DNA." PNAS 99(9): 6005-6010 Molecular Combing, herein incorporated by reference in its entirety.

Example 5

DNA Combing Protocol

DNA combing is preformed on silanized substrate essentially as described by Michalet, et al. (Sep. 5, 1997) "Dynamic Molecular Combing: Stretching the Whole Human Genome for High-Resolution Studies." Science 277(5331): 1518-1523, herein incorporate by reference in its entirety. A nucleic acid solution is placed into a 2 mL TEFLON reservoir and contacted with a silanized substrate for 5 minutes at room temperature. The substrate is removed from the reservoir at the speed of 300 μm/s.

DNA Combing by Capillary Flow

The nucleic acid (e.g., DNA) is mounted by a procedure similar to Lim, et al. (2001) "Shotgun optical maps of the whole *Escherichia coli* O157:H7 genome." Genome Res. 11: 1584-1593, herein incorporated by reference in its entirety. Column-purified DNA is diluted to ~100 pM in sterile TE buffer (10 mM Tris, 1 mM EDTA, pH 7.5). Glass slides are blown clean of dust with nitrogen and then passed through a propane torch flame to remove impurities and moisture. The purified DNA can be pre-stained with 300 pM of YOYO-1 iodide (Molecular Probes, Eugene, Oreg.), which is an intercalating dye that stains the DNA backbone and makes it possible for visualization. A modified coverslip is placed on the glass slide, and 8 it of the DNA diluted in the imaging buffer is pipetted onto the edge. The solution is drawn under the coverslip by capillary action. The strong capillary flow causes the DNA fragments to be stretched and aligned on the coverslip surface.

DNA Combing by force flow

In DNA Combing by force flow, a coated coverslip is placed over the glass slide with one edge touching the slide at an angle of 20°, and 7 μl of DNA in imaging buffer is pipetted onto the interface between the slide and the coverslip. By dropping the coverslip onto the slide, the DNA solution is pushed between the coverslip and the slide, resulting in a strong fluid flow, which causes the DNA fragments to be stretched and aligned on the coverslip surface.

The resultant substantially uniform nucleic acid fragments can be collected by washing, eluting, transfer, or removal. The substrate can be then heated to 95° C. for 10 minutes to denature the affinity ligand-affinity ligand receptor complex, once removed the substrate can be reused.

Example 6

DNA Combing Protocol

DNA combing is preformed on highly ordered pyrolitic graphite (HOPG) and atomically smooth AU(111) (e.g., nanomaterials) essentially as described by Mehta, et al. (November 2007) "Rapid Extension of Single and Double Stranded DNA on Atomically Flat Conductive Surfaces." IEEE Transactions on Nanotechnology 6(6): 734-736, herein incorporate by reference in its entirety. The strength of the interaction between the nucleic acid sample and the substrate can be controlled by using either coordinating ions or self-assembled molecular monolayers (SAMs).

DNA Combing on a HOPG Substrate

HOPG (SPI supplies) are cleaved using an adhesive tape and soaked in 10 mM $MgCl_2$ solution for 10 minutes prior to stretching the sample nucleic acids. The HOPG substrate is then reinsed with dionized water and dried in a flow of air. Five microliters of a nucleic acid solution (5 mm/mL, Tris-EDTA buffer, pH 7.8) is dispensed on the edge of the substrate. The droplet of nucleic acid solution is dragged at a rate of 0.05 mm/s (50 μm/s) using a syringe pump (New Era Syringe Pumps, NY) with a 18 mm×18 mm glass coverslip at a 90° angle to the HOPG substrate. The HOPG substrate is then rinsed with deionized water and air dried. Double-stranded DNA can be denatured to form single stranded DNA by heating the nucleic acid stretched on the HOPG substrate by heating at 95° C. for 5 minutes in 10 mM Tris, 0.1 EDTA buffer (TE buffer) at pH 7.8.

DNA Combing on an Atomically Smooth Au(111) Substrate

The surface charge density of the Au(111) substrate is controlled by forming mixed self-assembled molecular monolayers (SAMs) of neutral and positively charge molecules in a ratio (e.g., mixed SAMS containing mercaptoundecylamine:dodecanethiol in mole ratios of 0:1, 0.001:0.999, 0.01:0.99, 0.1; 0.9, and 1.0). Mixed SAMs containing mercaptudecylamine and dodecanethiol are prepared on Au(111) substrates with atomically flat terraces (Agilent Technologies, AFM) from a solution of both compounds in ethanol. The Au(111) substrate is rinsed with ethanol and dried in a vacuum dessicator. Five microliters of a nucleic acid solution (5 mm/mL, Tris-EDTA buffer, pH 7.8) is dispensed on the edge of the Au(111) substrate. The droplet of nucleic acid solution is dragged at a rate of 0.05 mm/s (50 µm/s) using a syringe pump (New Era Syringe Pumps, NY) with a 18 mm×18 mm glass coverslip at a 90° angle to the Au(111). The Au(111) can then rinsed with deionized water and air dried. Double-stranded DNA can be denatured to form single stranded DNA by heating the nucleic acid stretched on the Au(111) by heating at 95° C. for 5 minutes in 10 mM Tris, 0.1 EDTA buffer (TE buffer) at pH 7.8.

Example 7

DNA Combing Protocol

DNA combing (e.g., Chromosome Combing, molecular combing) may be used to produce an array of substantially uniformly stretched nucleic acids. In general, a substrate is coated with the octenyl carbon chain product of a gas-phase silanization reaction and is dipped into a buffered DNA solution. DNA strand ends bind to the hydrophobic surface in a pH-dependent manner and are stretched as the substrate is pulled from the solution at a constant speed, producing irreversibly fixed DNA strands aligned in parallel over the surface of the slide.

Generally, nucleic acids in solution (e.g., has a random-coil structure) are stretched by retracting the meniscus of the solution at a constant rate (e.g., at least about 100, 200, or 300 µm/s).

As the meniscus retracts, surface retention creates a force that acts on nucleic acid to retain it in the liquid phase; however this force is inferior to the strength of the nucleic acid attachment; the result is that the nucleic acid is stretched as it enters the air phase; as the force acts in the locality of the air/liquid phase, it is invariant to different lengths or conformations of the nucleic acid in solution, so nucleic acid of any length will be stretched the same as the meniscus retracts. As this stretching is constant along the length of a nucleic acid, distance along the strand can be related to base content (e.g., 1 µm is approximately equivalent to about 2 kb).

During the incubation, the DNA molecules become anchored on the surface by their ends. By extracting the surface from the reservoir, this has the same effect as the evaporation provided for in the "drop method," the meniscus moves relative to the surface and exerts a constant pulling force on the molecules remaining in the reservoir.

Example 8

Production of Substantially Uniform Nucleic Acid Fragments Using an Array

A substrate (e.g., array with at least one glass surface) is silanized according to the method described in Example 1 or 2. A plurality of nucleases are bound to regions separated by a pitch of at least 100 nm on the array (e.g., substrate) to form cleavage regions.

A nucleic acid sample comprising a linearized DNA library is contacted with the array comprising a silanized modified region and a plurality of cleavage regions separated by a pitch of at least 100 nm.

The substrate is subjected to a DNA combing procedure to stretch out the DNA molecules along the length of the array. The cleavage regions comprising bound DNAase I (e.g., nuclease) are activated by the addition of magnesium ($Mg^{2+}$) to allow DNAase I to cleave the bound DNA molecule into substantially uniform fragments. The substantially uniform DNA fragments are collected.

Example 9

Production of Substantially Uniform Nucleic Acid Fragments Using an Array with an Affinity-Ligand/Affinity Ligand Receptor A nucleic acid sample comprising a linearized DNA library is contacted with biotin (e.g., affinity ligand) to allow the formation of a DNA-biotin complex where the biotin is bound to one end of the DNA molecule.

An array with at least one glass surface is prepared by binding strepavidin to a region of the substrate to form a modified region. A plurality of nucleases are bound to regions separated by a pitch of at least 100 nm on the array (e.g., substrate) to form cleavage regions.

The DNA-biotin complex is contacted with substrate. The substrate is subjected to a DNA combing procedure to stretch out the DNA molecule along the length of the array. The cleavage regions comprising bound DNAase I (e.g., nuclease) are activated to allow DNAase to cleave the bound DNA molecule into substantially uniform fragments. The substantially uniform DNA fragments are collected. After two subsequent washes with a solution with a Tris-HCl (pH=7.0) buffer at room temperature for 15 minutes the substrate is subjected to conditions that disrupt the remaining bound affinity ligand-DNA/affinity ligand receptor complexes. A second set of two subsequent washes with a solution with a Tris-HCl (pH=7.0) buffer at room temperature for 15 minutes to wash off the liberated affinity ligand-DNA moieties. The substrate is then reused.

What is claimed is:

1. A method of generating nucleic acid fragments of substantially uniform length from one or more sample nucleic acids, comprising contacting one or more sample nucleic acids with an affinity ligand, linearly stretching the one or more sample nucleic acids over a substrate including a modified region comprising a plurality of affinity ligand receptors and a plurality of cleavage regions separated by relatively consistent distances, and cleaving the linearly stretched one or more sample nucleic acids with a chemical cleavage agent that is directly attached to the substrate at the cleavage regions or nuclease that is directly attached to the substrate at the cleavage regions.

2. A method of generating nucleic acid fragments of substantially uniform length from one or more sample nucleic acids, comprising linearly stretching the one or more nucleic acids over a substrate comprising a plurality of cleavage regions separated by relatively consistent distances, and cleaving the one or more linearly stretched sample nucleic acids with a chemical cleavage agent that is directly attached to the substrate at the cleavage regions or nuclease that is directly attached to the substrate at the cleavage regions, further comprising linearly stretching the one or more nucleic acids over the substrate by surface-tethered nucleic acid stretching, further comprising attaching a micron-size bead to the free end of the nucleic acid.

3. A method of generating nucleic acid fragments of substantially uniform length from one or more sample nucleic acids, comprising linearly stretching the one or more nucleic acids over a substrate comprising a plurality of cleavage regions separated by relatively consistent distances, and cleaving the one or more linearly stretched sample nucleic acids with a chemical cleavage agent that is directly attached to the substrate at the cleavage regions or nuclease that is directly attached to the substrate at the cleavage regions, further comprising linearly stretching the one or more nucleic acids over the substrate by surface-tethered nucleic acid stretching, further comprising attaching a magnetic bead to the nucleic acid and using magnets for the nucleic acid stretching.

4. The method of claim 2 or 3, comprising performing the surface-tethered nucleic acid stretching in parallel on a plurality of nucleic acid samples.

5. A method of generating nucleic acid fragments of substantially uniform length from one or more sample nucleic acids, comprising linearly stretching the one or more nucleic acids over a substrate comprising a plurality of cleavage regions separated by relatively consistent distances, and cleaving the one or more linearly stretched sample nucleic acids with a chemical cleavage agent that is directly attached to the substrate at the cleavage regions or nuclease that is directly attached to the substrate at the cleavage regions, wherein the linear stretching of the sample nucleic acid comprises a nucleic acid optical entrapment technique with an optically trapped particle attached to the sample nucleic acid.

6. The method of claim 5, comprising two optically trapped particles attached to the sample nucleic acid, one to each end.

7. A method of generating nucleic acid fragments of substantially uniform length from one or more sample nucleic acids, comprising linearly stretching the one or more nucleic acids over a substrate comprising a plurality of cleavage regions separated by relatively consistent distances, and cleaving the one or more linearly stretched sample nucleic acids with a chemical cleavage agent that is directly attached to the substrate at the cleavage regions or nuclease that is directly attached to the substrate at the cleavage regions, wherein the linear stretching of the sample nucleic acid comprises electrophoresis of nucleic acid.

8. A method of generating nucleic acid fragments of substantially uniform length from one or more sample nucleic acids, comprising linearly stretching the one or more nucleic acids over a substrate comprising a plurality of cleavage regions separated by relatively consistent distances, and cleaving the one or more linearly stretched sample nucleic acids with a chemical cleavage agent that is directly attached to the substrate at the cleavage regions or nuclease that is directly attached to the substrate at the cleavage regions, wherein the chemical cleavage agent comprises at least one chemical hydroxyl radical generator.

9. A method of generating nucleic acid fragments of substantially uniform length from one or more sample nucleic acids, comprising linearly stretching the one or more nucleic acids over a substrate comprising a plurality of cleavage regions separated by relatively consistent distances, and cleaving the one or more linearly stretched sample nucleic acids with a chemical cleavage agent that is directly attached to the substrate at the cleavage regions or nuclease that is directly attached to the substrate at the cleavage regions, wherein at least one of said one or more samples has a complexity of at least 1 Gbases.

10. The method of any one of claim 2, 3, 5, 7, 8 or 9, further comprising contacting one or more sample nucleic acids with an affinity ligand, wherein the substrate further includes a modified region comprising a plurality of affinity ligand receptors.

11. The method of any one of claim 2, 3, 5, 7, 8 or 9, further comprising collecting the resultant substantially uniform length nucleic acid fragment product.

12. The method of claim 11, further comprising sequencing the resultant substantially uniform length nucleic acid fragment product.

13. A method of generating nucleic acid fragments of substantially uniform length from one or more sample nucleic acids, comprising contacting one or more sample nucleic acids with an affinity ligand, linearly stretching the one or more sample nucleic acids over a substrate including a modified region comprising a plurality of affinity ligand receptors and a plurality of cleavage regions separated by relatively consistent distances, and cleaving the linearly stretched one or more sample nucleic acids with a chemical cleavage agent that is directly attached to the substrate at the cleavage regions or nuclease that is directly attached to the substrate at the cleavage regions, wherein the cleavage regions comprise an electrode.

14. A method of generating nucleic acid fragments of substantially uniform length from one or more sample nucleic acids, comprising contacting one or more sample nucleic acids with an affinity ligand, linearly stretching the one or more sample nucleic acids over a substrate including a modified region comprising a plurality of affinity ligand receptors and a plurality of cleavage regions separated by relatively consistent distances, and cleaving the linearly stretched one or more sample nucleic acids with a chemical cleavage agent that is directly attached to the substrate at the cleavage regions or nuclease that is directly attached to the substrate at the cleavage regions, wherein said cleavage regions are activatable.

15. The method of claim 13 or 14, further comprising collecting the resultant substantially uniform length nucleic acid fragment product.

16. The method of claim 15, further comprising sequencing the resultant substantially uniform length nucleic acid fragment product.

17. A method of sequencing nucleic acid, comprising linearly stretching one or more sample nucleic acids over a substrate comprising a plurality of cleavage regions separated by a uniform pitch, cleaving the linearly stretched one or more sample nucleic acids with a chemical cleavage agent that is directly attached to the substrate at the cleavage regions or nuclease that is directly attached to the substrate at the cleavage regions, thereby producing a substantially uniform length nucleic acid fragment pool, collecting the substantially uniform length nucleic acid fragment pool; and sequencing the resultant substantially uniform length nucleic acid fragment pool.

18. A method of sequencing nucleic acid, comprising linearly stretching one or more sample nucleic acids over a substrate comprising a plurality of cleavage regions separated by a uniform pitch, cleaving the linearly stretched one or more sample nucleic acids with a chemical cleavage agent that is directly attached to the substrate at the cleavage regions or nuclease that is directly attached to the substrate at the cleavage regions, thereby producing a substantially uniform length nucleic acid fragment pool, collecting the substantially uniform length nucleic acid fragment pool; and sequencing the resultant substantially uniform length nucleic acid fragment pool, wherein the cleavage regions comprise an electrode.

19. A method of sequencing nucleic acid, comprising linearly stretching one or more sample nucleic acids over a substrate comprising a plurality of cleavage regions separated by a uniform pitch, cleaving the linearly stretched one or more sample nucleic acids with a chemical cleavage agent that is directly attached to the substrate at the cleavage regions or nuclease that is directly attached to the substrate at the cleavage regions, thereby producing a substantially uniform length nucleic acid fragment pool, collecting the substantially uniform length nucleic acid fragment pool; and sequencing the resultant substantially uniform length nucleic acid fragment pool, wherein said cleavage regions are activatable.

* * * * *